United States Patent [19]

Kamiya et al.

[11] 4,407,798
[45] Oct. 4, 1983

[54] CEPHEM COMPOUNDS

[75] Inventors: Takashi Kamiya, Suita; Tsutomu Teraji, Osaka; Yoshiharu Nakai, Ōtsu; Kazuo Sakane, Amagasaki; Jiro Goto, Suita, all of Japan

[73] Assignee: Fujisawa Pharmaceutical Co., Ltd., Osaka, Japan

[21] Appl. No.: 296,301

[22] Filed: Aug. 26, 1981

[30] Foreign Application Priority Data

Aug. 29, 1980 [GB] United Kingdom ................. 8028042

[51] Int. Cl.³ ................. C07D 501/58; A61K 31/545
[52] U.S. Cl. ...................................... 424/246; 544/25
[58] Field of Search .................. 544/25; 424/246, 270

[56] References Cited

U.S. PATENT DOCUMENTS 4,079,178 3/1978 Cook et al. ........................... 544/25
4,258,041 3/1981 O'Callaghan et al. .............. 424/246
4,278,671 7/1981 Ochiai et al. ........................ 424/246

FOREIGN PATENT DOCUMENTS 2010840A 7/1979 United Kingdom ................ 424/246

Primary Examiner—Nicholas S. Rizzo
Attorney, Agent, or Firm—Oblon, Fisher, Spivak, McClelland & Maier

[57] ABSTRACT

This invention relates to novel compounds having antimicrobial activity of the formula

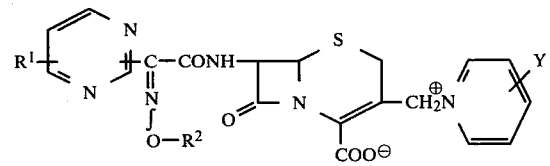

in which
R¹ is amino or a protected amino group,
R² is cyclo(lower)alkyl, cyclo(lower)alkenyl, lower alkyl, lower alkynyl, carboxy(lower)alkyl, protected carboxy(lower)alkyl or lower alkylthio(lower)alkyl, and
Y is hydrogen, amino or a protected amino group, and pharmaceutically acceptable salts thereof.

13 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compound is novel and can be represented by the following general formula (I).

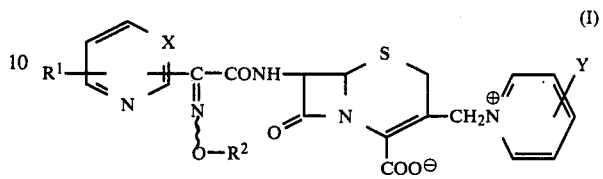

in which
$R^1$ is amino or a protected amino group,
$R^2$ is an aliphatic hydrocarbon residue which may have suitable substituent(s),
X is N or CH, and
Y is hydrogen, amino or a protected amino group.

According to the present invention, the new cephem compound (I) can be prepared by various processes which are illustrated in the following scheme.

(1) Process 1:

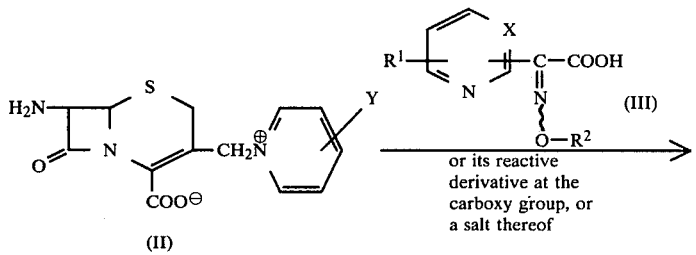

(II)

or its reactive derivative at the amino group, or a salt thereof or its reactive derivative at the carboxy group, or a salt thereof

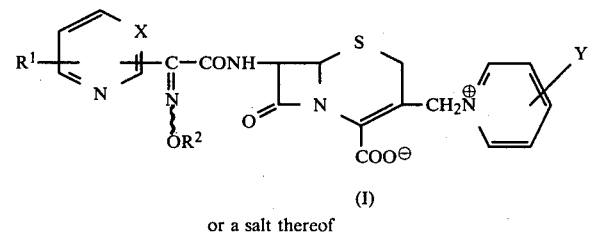

(I)

or a salt thereof (2) Process 2:

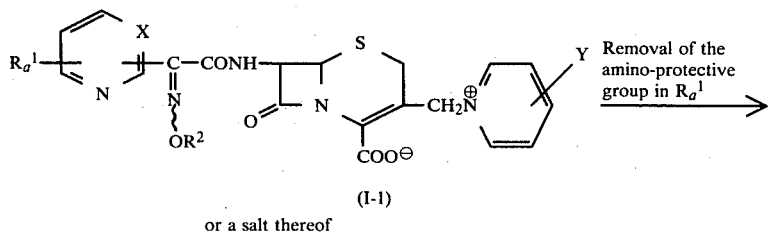

(I-1)

or a salt thereof

Removal of the amino-protective group in $R_a^1$

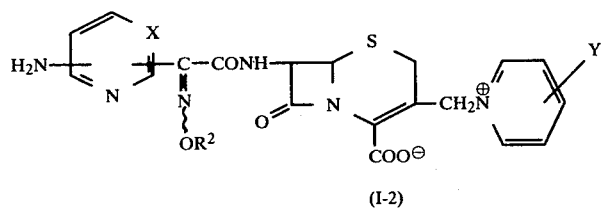
(I-2)
or a salt thereof
(3) Process 3:
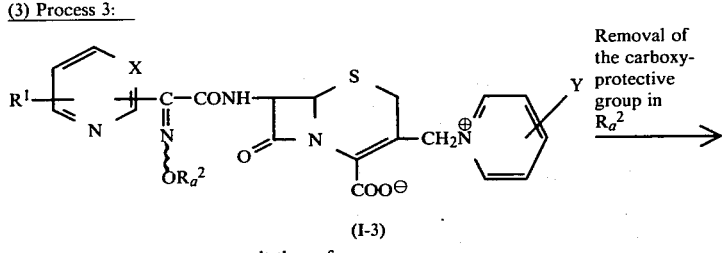
(I-3)
or a salt thereof
Removal of the carboxy-protective group in $R_a^2$ →
(I-4)
or a salt thereof
(4) Process 4:
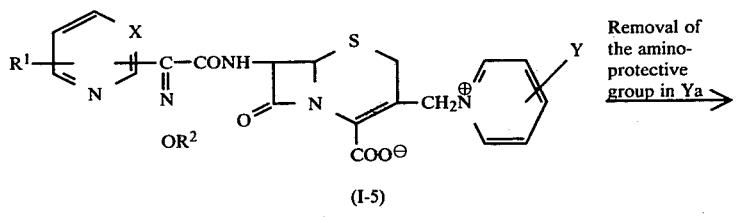
(I-5)
or a salt thereof
Removal of the amino-protective group in Ya →
(I-6)
or a salt thereof
(5) Process 5:
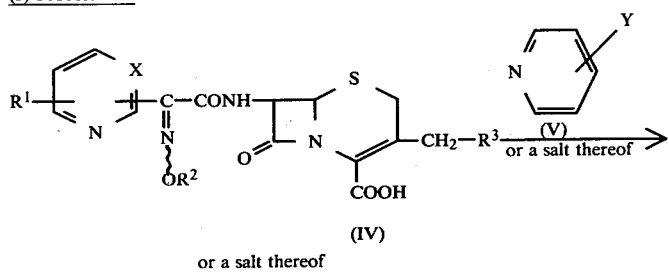
(IV)
or a salt thereof
$\xrightarrow{(V)}{\text{or a salt thereof}}$ -continued

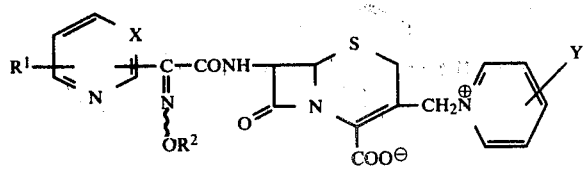

(I)

or a salt thereof wherein
R$^1$, R$^2$, Y and X are each as defined above,
R$_a^1$ is a protected amino group,
R$_a^2$ is lower alkyl having a protected carboxy group,
R$_b^2$ is lower alkyl having carboxy,
Y$_a$ is protected amino group and
R$^3$ is a group which can be substituted with a group of the formula:

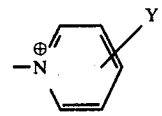

wherein Y is as defined above.

Some of the starting compound (III) and (IV) can be prepared by the method in the following reaction scheme.

Process A

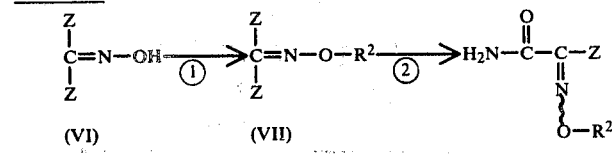

(VI)          (VII)          (VIII)

or a salt thereof

Process B

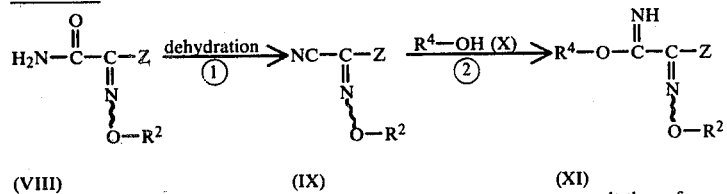

(VIII)         (IX)          (XI)
                              or a salt thereof

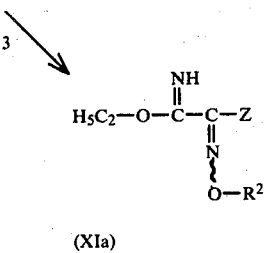

(XIa)

or a salt thereof

Process C

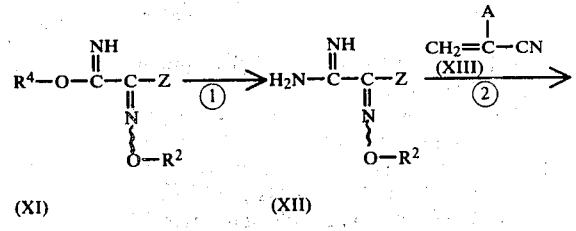

(XI)          (XII)
or a salt thereof    or a salt thereof

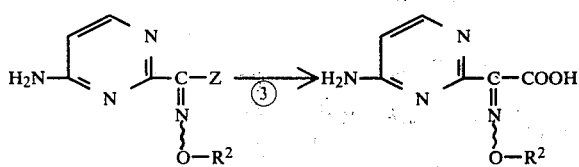

(XIV)

or a salt thereof (IIIa)

or a salt thereof

Process D

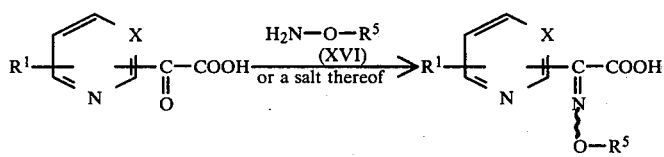

(XV)

or a salt thereof (IIIb)

or a salt thereof

Process E

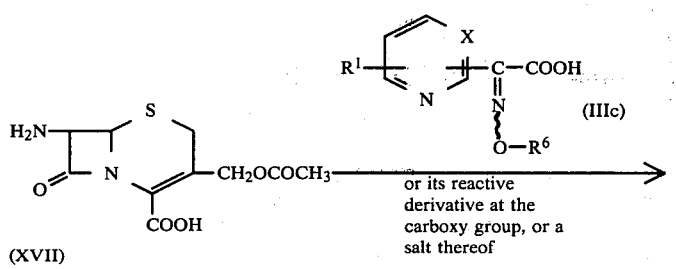

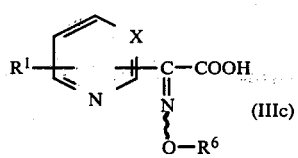

(XVII)

or its reactive
derivative at the
amino group, or
a salt thereof

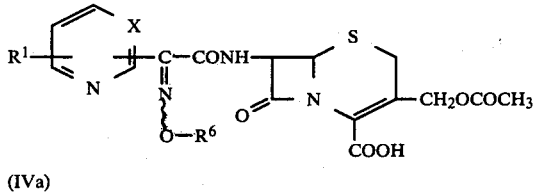

(IVa)

or a salt thereof wherein
$R^1$, $R^2$ and X are each as defined above,
Z is a protected carboxy group,
$R^4$ is lower alkyl,
A is halogen,
$R^5$ is ethyl, cyclo(lower)alkyl, cyclo(lower)alkenyl, lower alkyl having a protected carboxy group, lower alkynyl or lower alkylthio(lower)alkyl, and
$R^6$ is lower alkynyl,
provided that X is N when $R^5$ is lower alkynyl and $R^1$ is amino when $R^5$ is ethyl.

In the present invention, with regard to the object compound (I), (I-2), (I-4) and (I-6), the starting compounds (III), (I-1), (I-3), (I-5) and (IV) and the other compounds (VIII), (IX), (XI), (XIa), (XII), (XIV), (IIIa), (IIIb), (IIIc) and (IVa), it is to be understood that all of said compounds include syn isomer, anti isomer and a mixture thereof. And, as to the object compound (I), the syn isomer thereof means one geometrical isomer having the group represented by the following formula:

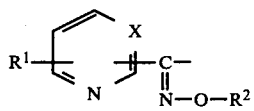

(wherein $R^1$, $R^2$ and X are each as defined above). and the anti isomer means the other geometrical isomer having the group of the formula:

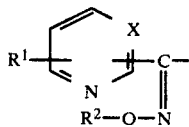

(wherein $R^1$, $R^2$ and X are each as defined above). And, as to the compound (VIII), the syn isomer thereof means one geometrical isomer having the group represented by the following formula:

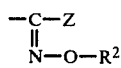

(wherein $R^2$ and Z are each as defined above). and the anti isomer means the other geometrical isomer having the group of the formula:

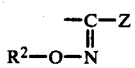

(wherein $R^2$ and Z are each as defined above). Further, as to the other compounds, the syn and anti isomers thereof also are represented by the same geometrical configuration as that of the compound (I) or (VIII), respectively.

Suitable pharmaceutically acceptable salts of the object compounds (I) are conventional non-toxic salts and may include a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with an amino acid (e.g. aspartic acid, glutamic acid, etc.); and the like.

In the above and subsequent description of the present invention, suitable examples and illustration of the various definitions to be included within the scope thereof are explained in detail as follows.

The term "lower" in the present specification is intended to mean a group having 1 to 6 carbon atoms, unless otherwise indicated.

Suitable "amino-protective group" in the term "a protected amino group" may include conventional one which is used in penicillin and cephalosporin compounds, for example, acyl as mentioned below, mono to triphenyl(lower)alkyl (e.g. benzyl, phenethyl, benzhydryl, trityl, etc.), lower alkoxycarbonyl(lower)alkylidene or its enamine tautomer (e.g. 1-methoxycarbonyl-1-propen-2-yl, etc.), di(lower)alkylaminomethylene (e.g. dimethylaminomethylene, etc.), etc.

Suitable "acyl" may include an aliphatic acyl, an aromatic acyl, a heterocyclic acyl and an aliphatic acyl substituted with aromatic or heterocyclic group(s).

The aliphatic acyl may include saturated or unsaturated, acyclic or cyclic ones, such as lower alkanoyl (e.g. formyl, acetyl, propionyl, butyryl, isobutyryl, valeryl, isovaleryl, pivaloyl, hexanoyl, etc.), lower alkanesulfonyl (e.g. mesyl, ethanesulfonyl, propanesulfonyl, etc.), lower alkoxycarbonyl (e.g. methoxycarbonyl, ethoxycarbonyl, propoxycarbonyl, butoxycarbonyl, tert-butoxycarbonyl, etc.), lower alkenoyl (e.g. acryloyl, methacryloyl, crotonoyl, etc.), ($C_3$-$C_7$)-cycloalkanecarbonyl (e.g. cyclohexanecarbonyl, etc.), and the like.

The aromatic acyl may include aroyl (e.g. benzoyl, toluoyl, xyloyl, etc.), arenesulfonyl (e.g. benzenesulfonyl, tosyl, etc.), and the like.

The heterocyclic acyl may include heterocyclecarbonyl (e.g. furoyl, thenoyl, nicotinoyl, isonicotinoyl, thiazolylcarbonyl, thiadiazolylcarbonyl, tetrazolylcarbonyl, etc.), and the like.

The aliphatic acyl substituted with aromatic group(s) may include phenyl(lower)alkanoyl (e.g. phenylacetyl, phenylpropionyl, phenylhexanoyl, etc.), phenyl(lower)alkoxycarbonyl (e.g. benzyloxycarbonyl, phenethyloxycarbonyl, etc.), phenoxy(lower)alkanoyl (e.g. phenoxyacetyl, phenoxypropionyl, etc.), and the like.

The aliphatic acyl substituted with heterocyclic group(s) may include thienylacetyl, imidazolylacetyl, furylacetyl, tetrazolylacetyl, thiazolylacetyl, thiadiazolylacetyl, thienylpropionyl, thiadiazolylpropionyl, and the like.

These acyl groups may be further substituted with one or more suitable substituents such as lower alkyl (e.g. methyl, ethyl, propyl, isopropyl, butyl, pentyl, hexyl, etc.), halogen (e.g. chlorine, bromine, iodine, fluorine), lower alkoxy (e.g. methoxy, ethoxy, propoxy, isopropoxy, butoxy, pentyloxy, hexyloxy, etc.), lower alkylthio (e.g. methylthio, ethylthio, propylthio, isopropylthio, butylthio, pentylthio, hexylthio, etc.), nitro and the like, and preferable acyl having such substituent(s) may be mono (or di or tri)halo(lower)alkanoyl (e.g. chloroacetyl, bromoacetyl, dichloroacetyl, trifluoroacetyl, etc.), mono (or di or tri)halo(lower)alkoxycarbonyl (e.g. chloromethoxycarbonyl, dichloromethoxycarbonyl, 2,2,2-tri-chloroethoxycarbonyl, etc.), nitro (or halo or lower alkoxy)phenyl(lower)alkoxycarbonyl (e.g. nitrobenzyloxycarbonyl, chlorobenzyloxycarbonyl, methoxybenzyloxycarbonyl, etc.), and the like.

The preferred embodiment of the amino-protective group thus defined is lower alkanoyl.

Suitable "protected carboxy group" may include an esterified carboxy group which is conventionally used in penicillin or cephalosporin compounds.

Suitable "ester moiety" in "esterified carboxy group" may include lower alkyl ester (e.g., methyl ester, ethyl ester, propyl ester, isopropyl ester, butyl ester, isobutyl ester, t-butyl ester, pentyl ester, tert-pentyl ester, hexyl ester, etc.), lower alkenyl ester (e.g. vinyl ester, allyl ester, etc.), lower alkynyl ester (e.g. ethynyl ester, propynyl ester, etc.), lower alkoxy(lower)alkyl ester (e.g. methoxymethyl ester, ethoxymethyl ester, isopropoxymethyl ester, 1-methoxyethyl ester, 1-ethoxyethyl ester, etc.), lower alkylthio(lower)alkyl ester (e.g. methylthiomethyl ester, ethylthiomethyl ester, ethylthioethyl ester isopropylthiomethyl ester, etc.), mono(or di or tri)halo(lower)alkyl ester (e.g. 2-iodoethyl ester, 2,2,2-trichloroethyl ester, etc.), lower alkanoyloxy(lower)alkyl ester (e.g. acetoxymethyl ester, propionyloxymethyl ester, butyryloxymethyl ester, isobutyryloxymethyl ester, valeryloxymethyl ester, pivaloyloxymethyl ester, hexanoyloxymethyl ester, 2-acetoxyethyl ester, 2-propionyloxyethyl ester, 1-acetoxypropyl ester, etc.), lower alkanesulfonyl(lower)alkyl ester (e.g. mesylmethyl ester, 2-mesylethyl ester, etc.), mono(or di or tri)phenyl(lower)alkyl ester which may have one or more suitable substituent(s) (e.g. benzyl ester, 4-methoxybenzyl ester, 4-nitrobenzyl ester, phenethyl ester, benzhydryl ester, trityl ester, bis(methoxyphenyl)methyl ester, 3,4-dimethoxybenzyl ester, 4-hydroxy-3,5-di-t-butylbenzyl ester, etc.), aryl ester which may have one or more suitable substituents (e.g. phenyl ester, tolyl ester, t-butylphenyl ester, xylyl ester, mesityl ester, cumenyl ester, salicyl ester, etc.), heterocyclic ester (e.g. phthalidyl ester, etc.), and the like, in which the preferred one is lower alkyl ester such as lower alkoxycarbonyl.

Suitable "an aliphatic hydrocarbon residue which may have suitable substituent(s)" may include lower alkyl which may have lower alkylthio, carboxy or a protected carboxy group as mentioned above; lower alkenyl; lower alkynyl; cyclo(lower)alkyl; cyclo(lower)alkenyl and the like.

Suitable "lower alkyl" and "lower alkyl moiety" in the terms "lower alkyl which may have lower alkylthio, carboxy or a protected carboxy group", "lower alkylthio", "lower alkylthio(lower)alkyl", "lower alkyl having a protected carboxy group" and "lower alkyl having carboxy" may include straight or branched one such as methyl, ethyl, propyl, isopropyl, butyl, isobutyl, pentyl, isopentyl, neopentyl, hexyl, or the like, in which the preferred one is $C_1$-$C_4$ alkyl.

Suitable "lower alkenyl" group may include straight or branched one such as vinyl, 1-propenyl, allyl, 1-(or 2- or 3-)butenyl, 1-(or 2- or 3- or 4-)pentenyl, 1-(or 2- or 3- or 4- or 5-)hexenyl, 2-methyl-2-propenyl, and the like, in which the preferred one is $C_2$-$C_5$ alkenyl.

Suitable "lower alkynyl" group may include straight or branched one such as propargyl, 2-(or 3-)butynyl, 2-(or 3- or 4-)pentynyl, 2-(or 3- or 4- or 5-)hexynyl, and the like, in which the preferred one is $C_2$-$C_5$ alkynyl.

Suitable "cyclo(lower)alkyl" may include cyclopropyl, cyclobutyl, cyclopentyl, cyclohexyl, and the like.

Suitable "cyclo(lower)alkenyl" may include cyclopropenyl, cyclobutenyl, cyclopentenyl, cyclohexenyl, and the like.

Suitable halogen may be chlorine, bromine, iodine, or fluorine.

Suitable $R^3$ may include an acid residue such as acyloxy, halogen (e.g. chlorine, bromine, iodine or fluorine), azido or the like, wherein acyl moiety in the term "acyloxy" can be referred to the ones as exemplified above.

Preferred embodiments of the object compounds (I) are as follows.

Preferred embodiment of $R^1$ is amino or acylamino (more preferably lower alkanoylaino);

$R^2$ is cyclo(lower)alkyl, cyclo(lower)alkenyl, lower alkyl, lower alkynyl, carboxy(lower)alkyl, esterified carboxy(lower)alkyl [more preferably lower alkoxycarbonyl(lower)alkyl] or lower alkylthio(lower)alkyl;

X is N or CH; and

Y is hydrogen, amino or acylamino (more preferably lower alkanoylamino).

The processes 1 to 5 for the preparation of the object compounds (I) of the present invention are explained in detail in the following.

(1) Process 1:

The compounds (I) or a salt thereof can be prepared by reacting the compound (II) or its reactive derivative at the amino group, or a salt thereof with the compound (III) or its reactive derivative at the carboxy group, or a salt thereof.

Suitable salts of the starting compound (II) may include the same acid addition salts as exemplified for the compounds (I).

Suitable salts of the starting compound (III) may include the same ones as exemplified for the compounds (I).

Suitable reactive derivative at the amino group of the compound (II) may include a conventional one, for example, a silyl derivative formed by the reaction of the compound (II) with a silyl compound such as bis-(trimethylsilyl)acetamide, trimethylsilylacetamide, etc.; isocyanate; isothiocyanate; Schiff's base or its tautomeric enamine type isomer formed by the reaction of the amino group with a carbonyl compound such as an aldehyde compound (e.g. acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde, etc.) or a ketone compound (e.g. acetone, methyl ethyl ketone, methyl isobutyl ketone, acetylacetone, ethyl acetoacetate, etc.), and the like.

Suitable reactive derivative at the carboxy group of the compound (III) may include, for example, an acid halide, an acid anhydride, an activated amide, an activated ester, and the like, and preferably an acid chloride and acid bromide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g. methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g. benzoic acid, etc.); a symmetrical acid anhydride; an activated acid amide with a heterocyclic compound containing imino function such as imidazole, 4-substituted imidazole, dimethylpyrazole, triazole or tetrazole; an activated ester (e.g. p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N-dimethylhydroxylamine, 1-hydroxy-2-(1H)-pyridone, N-hydroxysuccinimide, N-hydroxyphthalimide, 1-hydroxybenzotriazole, 1-hydroxy-6-chlorobenzotriazole, etc.), and the like.

The suitable reactive derivative can optionally be selected from the above according to the kinds of the compounds (II) and (III) to be used practically.

This reaction can be carried out in the presence of an organic or inorganic base such as alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, picoline, etc.), quinoline, and the like.

In case that the compound (III) is used in a form of the free acid or a salt in this reaction, the reaction is preferably carried out in the presence of a condensing agent such as a carbodiimide compound [e.g. N,N'-dicyclohexylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.], a ketenimine compound (e.g. N,N'-carbonylbis(2-methylimidazole), pentamethyleneketene-N-cyclohexylimine, diphenylketene-N-cyclohexylimine, etc.); an olefinic or acetylenic ether compounds (e.g. ethoxyacetylene, β-chlorovinylethyl ether), a sulfonic acid ester of N-hydroxybenzotriazole derivative [e.g. 1-(4-chlorobenzenesulfonyloxy)-6-chloro-1H-benzotriazole, etc.], a combination of trialkylphosphite or triphenylphosphine and carbon tetrachloride, disulfide or diazenedicarboxylate (e.g. diethyl diazenedicarboxylate, etc.), a phosphorus compound (e.g. ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as dimethylformamide, N-methylformamide or the like with a halogen compound such as thionyl chloride, phosphorus oxychloride, phosgene or the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

Among these solvents, hydrophilic solvents may be used in a mixture with water.

The reaction temperature is not critical and the reaction is usually carried out under cooling to warming.

The compounds (I) thus obtained can be used as the starting compound of the subsequent processes without any isolation.

(2) Process 2:

The compound (I-2) or a salt thereof can be prepared by subjecting the compound (I-1) or a salt thereof to removal reaction of the amino-protective group in $R_a^1$.

Suitable method for this removal reaction may include conventional one such as hydrolysis, reduction, combined methods comprising iminohalogenation and then iminoetherification, followed by hydrolysis, if necessary, and the like.

(i) For Hydrolysis:

Hydrolysis is preferably carried out in the presence of an acid.

Suitable acid may be an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, etc.), an acidic ion-exchange resin and the like. In case that the organic acid such as trifluoroacetic acid and p-toluenesulfonic acid is used in this reaction, the reaction is preferably carried out in the presence of cation trapping agents (e.g. anisole, etc.).

The acid suitable for this hydrolysis can be selected according to the kinds of the protective group to be removed, for example, this hydrolysis can preferably be applied to the amino-protective group for $R_a^1$ such as substituted or unsubstituted lower alkoxycarbonyl, substituted or unsubstituted lower alkanoyl.

The hydrolysis is usually carried out in a conventional solvent which does not adversely influence the reaction such as water, methanol, ethanol, propanol, tert-butyl alcohol, tetrahydrofuran, N,N-dimethylformamide, dioxane or a mixture thereof, and further the above-mentioned acids can also be used as a solvent when they are in liquid.

The reaction temperature of this hydrolysis is not critical, and the reaction is usually carried out under cooling to at somewhat elevated temperature.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like.

The reduction manner can be selected according to the kinds of the protective group to be removed, for example, the chemical reduction can preferably be applied to the amino-protective group for $R_a^1$ such as halo(lower)alkoxycarbonyl and the like, and catalytic reduction can preferably be applied to that such as substituted or unsubstituted ar(lower)alkoxycarbonyl, and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

(iii) For combined methods comprising iminohalogenation (the first step) and then iminoetherification (the 2nd step), followed by hydrolysis (the last step), if necessary:

The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps are usually conducted under cooling to at ambient temperature. These two steps and the last step (i.e. hydrolysis step) are most preferably conducted in one-batch system.

Suitable iminohalogenating agents include a halogenating agent such as phosphorus halo compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like.

Thus obtained reaction product is, if necessary, hydrolyzed in a conventional manner. The hydrolysis is preferably carried out at ambient temperature to under cooling, and preceeds simply pouring the reaction mixture into water or a hydrophilic solvent such as alcohol (e.g. methanol, ethanol, etc.) moistened or admixed with water, and if necessary, with addition of an acid or base.

Suitable acid may include the same ones as those given in the explanation of Hydrolysis mentioned in the above item (i), and suitable base may include the same ones as those given in the explanation of Process 1.

The methods thus explained may be selected depending upon the kind of the protective groups to be removed.

The present invention includes, within the scope of the invention, the cases that the protected carboxy group in $R^2$ and/or the protected amino group in Y are transformed into the free carboxy group and/or free amino group during the reaction and post-treatment of the reaction.

The compound (I-2) thus obtained can be used as the starting compound of the subsequent process without any isolation.

(3) Process 3:

The compound (I-4) or a salt thereof can be prepared by subjecting the compound (I-3) or a salt thereof to removal reaction of the carboxy-protective group in $R_a^2$.

This reaction is carried out by a conventional method such as hydrolysis, reduction, and the like.

The method of hydrolysis and reduction, and the reaction conditions (e.g. reaction temperature, solvent, etc.) are substantially the same as those illustrated for the removal reaction of the amino-protective group of the compound (I-1) in Process 2, and therefore are to be referred to said explanation.

The compound (I-4) thus obtained can be used as the starting compound of the subsequent process without any isolation.

(4) Process 4:

The compound (I-6) or a salt thereof can be prepared by subjecting the compound (I-5) or a salt thereof to removal reaction of the amino-protective group in Ya.

This reaction is carried out in a similar manner to that of Process 2 as mentioned above.

(5) Process 5:

The object compound (I) or a salt thereof can be prepared by reacting the compound (IV) or a salt thereof with the compound (V) or a salt thereof.

Suitable salt of the compound (IV) can be referred to the ones as exemplified for the compound (I).

Suitable salt of the compound (V) can be referred to the acid addition salt as exemplified for the compound (I).

The present reaction may be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IV) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under heating. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc.

The process A to E for the preparation of some of the starting compounds (III) and (IV) of the present invention are explained in detail in the following.

Process A- ①

The compound (VII) can be prepared by subjecting the compound (VI) or a salt thereof to introduction reaction of the aliphatic hydrocarbon residue which may have suitable substituent(s) on hydroxyimino group.

Suitable salt of the compound (VI) may include an alkali metal salt (e.g., sodium salt, potassium salt), and the like. The suitable reagent for the present reaction may include mono or di(lower)alkyl sulfate (e.g., methyl sulfate, dimethyl sulfate, diethyl sulfate, etc.), aliphatic hydrocarbon halide (e.g. methyl iodide, ethyl iodide, cyclopentyl chloride, allyl bromide, propargyl bromide, etc.), diazomethane and the like.

The reaction using mono or di(lower)alkyl sulfate is preferably carried out in the presence of a base, for example, an inorganic base such as an alkali metal hydroxide (e.g., sodium hydroxide, potassium hydroxide etc.), an alkali metal bicarbonate (e.g., sodium bicarbonate, potassium bicarbonate, etc.) or an alkali metal carbonate (e.g., sodium carbonate, potassium carbonate, etc.), an organic base such as an alkali metal alkoxide (e.g., sodium methoxide, sodium ethoxide etc.), a trialkylamine (e.g. trimethylamine, triethylamine, etc.), triethanolamine, N,N-dimethylaniline, N,N-dimethylbenzylamine, N-methylmorpholine or pyridine, or the like.

The present reaction is usually carried out in a solvent such as water, acetone, alcohol (e.g., methanol, ethanol, etc.), ether, ethyl acetate, dimethylformamide or any other solvent which does not adversely affect the reaction.

The reaction temperature is not critical and the reaction is usually carried out under cooling to heating.

Process A- ②

The compound (VIII) can be prepared by reacting the compound (VII) with ammonia. The present reaction is usually carried out in a solvent such as water, alcohol (e.g., methanol, ethanol, etc.) or any other solvent which does not adversely affect the reaction. The reaction temperature is not critical and the reaction is usually carried out under cooling to heating.

Process B- ①

The compound (IX) can be prepared by subjecting the compound (VIII) to dehydration.

The dehydrating agent to be used in this dehydration reaction may include phosphoryl chloride, thionyl chloride, phosphorus pentoxide, phosphorus pentachloride, phosphorus pentabromide, acetic anhydride, trifluoroacetic anhydride and the like.

The present reaction is usually carried out in a solvent such as dioxane, chloroform, methylene chloride, 1,2-dichloroethane, tetrahydrofuran, pyridine, acetonitrile, dimethylformamide or any other solvent which does not adversely affect the reaction.

The reaction temperature is not critical and the reaction is usually carried out under cooling to heating.

Process B- ②°

The compound (XI) or a salt thereof can be prepared by reacting the compound (IX) with the compound (X).

Suitable salt of the compound (XI) may include the same acid addition salt as exemplified for compound (I).

The present reaction is usually carried out in the presence of an organic or inorganic base as exemplified in Process 1.

The reaction is usually carried out in a solvent which does not adversely affect the reaction, and when the compound (X) is liquid, the compound (X) can also be used as solvent.

The reaction temperature is not critical and the reaction is usually carried out under cooling to heating.

Process B- ③

The compound (XIa) or a salt thereof can be prepared by reacting the compound (VIII) with Meerwein reagent (triethyloxonium tetrafluoroborate).

Suitable salt of the compound (XIa) may include the same acid addition salt as exemplified for compound (I).

The present reaction is usually carried out in a solvent such as methylene chloride or any other solvent which does not adversely affect the reaction. The reaction temperature is not critical and the reaction is usually carried out under cooling to warming.

Process C- ①

The compound (XII) or a salt thereof can be prepared by reacting the compound (XI) or a salt thereof with ammonium salt.

Suitable ammonium salt may include ammonium acetate, ammonium sulfate, ammonium halide (e.g., ammonium chloride, ammonium bromide, etc.), and the like.

Suitable salt of the compound (XII) may include the same acid addition salt as exemplified for the compound (I).

The present reaction is usually carried out in a solvent such as alcohol (e.g., methanol, ethanol, etc.), acetone, chloroform, dimethylformamide, dimethylsulfoxide, acetonitrile, tetrahydrofuran, or any other solvent which does not adversely affect the reaction.

The reaction temperature is not critical and the reaction is usually carried out under cooling to heating.

Process C- ②

The compound (XIV) or a salt thereof can be prepared by reacting the compound (XII) or a salt thereof with the compound (XIII).

Suitable salt of the compound (XIV) may include the same acid addition salt as exemplified for the compound (I).

The present reaction is usually carried out in the presence of a base as aforementioned in Process 1.

The present reaction is usually carried out in a solvent such as alcohol (e.g., methanol, ethanol, etc.), acetone, N,N-dimethylformamide or any other solvent which does not adversely affect the reaction.

The reaction temperature is not critical and the reaction can be carried out under cooling to heating.

Process C- ③

The object compound (IIIa) or a salt thereof can be prepared by subjecting the compound (XIV) or a salt thereof to elimination reaction of the protective group of carboxy.

Suitable salt of the compound (IIIa) may include the same one as exemplified for the compound (I).

The present reaction is carried out in accordance with a conventional method such as hydrolysis, reduction or the like.

In case that the protective group is an ester, the protective group can be eliminated by hydrolysis. Hydrolysis is preferably carried out in the presence of a base or an acid. Suitable base may include an inorganic base and an organic base such as an alikali metal (e.g. sodium, potassium, etc.), an alkaline earth metal (e.g. magnesium, calcium, etc.), the hydroxide or carbonate or bicarbonate thereof, trialkylamine (e.g. trimethylamine, triethylamine, etc.), picoline, 1,5-diazabicyclo[4,3,0]-none-5-ene, 1,4-diazabicyclo[2,2,2]octane, 1,8-diazabicyclo[5,4,0]undecene-7, or the like. Suitable acid may include an organic acid (e.g. formic acid, acetic acid, propionic acid, trifluoroacetic acid, etc.) and an inorganic acid (e.g. hydrochloric acid, hydrobromic acid, sulfuric acid, etc.). The acidic hydrolysis using trifluoroacetic acid is usually accelerated by addition of anisole.

The reaction is usually carried out in a solvent such as water, methylene chloride, an alcohol (e.g. methanol, ethanol, etc.), a mixture thereof or any other solvent which does not adversely influence the reaction. A liquid base or acid can also be used as the solvent. The reaction temperature is not critical and the reaction is usually carried out under cooling to warming.

Reduction can be applied preferably for elimination of the protective group such as 4-nitrobenzyl, 2-iodoethyl, 2,2,2-trichloroethyl, or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst (e.g. palladium-carbon, etc.).

Process D

The compound (IIIb) or a salt thereof can be prepared by reacting the compound (XV) or a salt thereof with the compound (XVI) or a salt thereof.

Suitable salt of the compound (XVI) may include the same acid addition salt as exemplified for the compound (I).

Suitable salts of the compound (XV) and (IIIb) may include the same ones as exemplified for the compound (I)

When the compound (XVI) is used as its salt form, the reaction is preferably carried out in the presence of a base as exemplified in Process 1.

This reaction is usually carried out in a conventional solvent which does not adversely influence the reaction such as water, methanol, ethanol, propanol, dioxane, tetrahydrofuran, etc., or a mixture thereof.

The reaction temperature is not critical and the reaction is usually carried out under cooling to warming.

Process E

The compound (IVa) or a salt thereof can be prepared by reacting the compound (XVII) or its derivative at the amino group or a salt thereof with the compound (IIIc) or its reactive derivative at the carboxy group or a salt thereof.

Suitable salts of the compound (IVa), (XVII) and (IIIc) may include the same ones as exemplified for the compound (I).

The reaction may be conducted substantially in the same manner as aforementioned Process 1.

In case that the object compounds (I) have a free carboxy group or a free amino group, it may be transformed into its pharmaceutically acceptable salts by a conventional method.

The object compounds (I) and the pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compounds (I), the test data on the in vitro antimicrobial activity of some representative compounds (I) of this invention are shown in the following. Test: In vitro Antimicrobial Activity.

| Test Compounds | |
|---|---|
| No. 1 | 7-[2-Cyclopentyloxyimino-2-(4-aminopyrimidin-2-yl)acetamido]-3-(1-pyridiniomethyl)-3-cephem-4-carboxylate (syn isomer) (hereinafter referred to as Compound A). |
| No. 2 | 7-[2-Methylthiomethoxyimino-2-(4-aminopyrimidin-2-yl)acetamido]-3-(1-pyridiniomethyl)-3-cephem-4-carboxylate (syn isomer) (hereinafter referred to as Compound B). |
| No. 3 | 7-[2-Ethoxyimino-2-(4-aminopyrimidin-2-yl)-acetamido]-3-(1-pyridiniomethyl)-3-cephem-4-carboxylate (syn isomer) (hereinafter referred to as Compound C). |
| No. 4 | 7-[2-(Propargyloxyimino-2-(4-aminopyrimidin-2-yl)acetamido]-3-(1-pyridiniomethyl)-3-cephem-4-carboxylate (syn isomer) (hereinafter referred to as Compound D). |

Test Method

In vitro Antimicrobial activity was determined by the two-fold agar-plate dilution method as described below.

One loopful of an overnight culture of each test strain in Tripticase-soy broth (approximately $10^8$ viable cells per ml) was streaked on heart infusion agar (HI-agar) containing graded concentrations of antimicrobial agents, and the minimal inhibitory concentration (MIC) was expressed in term of µg/ml after incubation at 37° C. for 20 hours.

| Test Results MIC (µg/ml) | |
|---|---|
| Test compounds | Microorganisms Escherichia coli 31 |
| A | 0.05 |
| B | 0.05 |

| Test Results MIC (µg/ml) -continued | |
|---|---|
| Test compounds | Microorganisms Escherichia coli 31 |
| C | 0.05 |
| D | 0.05 |

For therapeutic administration, the object compounds (I) and the pharmaceutically acceptable salts thereof of the present invention are used in the form of conventional pharmaceutical preparation which contains said compound, as active ingredients, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade and the like. If needed, there may be included in the above preparations auxiliary substances, stabilizing agents, wetting agents and other commonly used additives such as lactose, magnesium stearate, terra alba, sucrose, corn starch, talc, stearic acid, gelatin, agar, pectin, peanut oil, olive oil, cacao butter, ethylene glycol and the like.

While the dosage of the compounds (I) may vary from and also depend upon the age, conditions of the patient, a kind of diseases, a kind of the compounds (I) to be applied, etc. In general, amounts between 1 mg and about 4,000 mg or even more per day may be administered to a patient. An average single dose of about 50 mg, 100 mg, 250 mg, 500 mg, 1000 mg, 2000 mg of the object compounds (I) of the present invention may be used in treating diseases infected by pathogenic microorganisms.

The following preparations and examples are given for the purpose of illustrating the present invention.

PREPARATION OF THE STARTING COMPOUNDS

Preparation 1

To a suspension of S-methyl (4-formamidopyrimidin-2-yl)thioglyoxylate (2.25 g) in water (25 ml) was added 1 N aqueous sodium hydroxide (9 ml), followed by stirring at ambient temperature for 25 minutes to produce a solution containing sodium (4-formamidopyrimidin-2-yl)glyoxylate.

On the other hand, a mixture of N-cyclopentyloxyphthalimide (2.77 g) and hydrazine monohydrate (0.57 g) in ethanol (14 ml) was refluxed under heating for 5 minutes and then cooled in an ice-bath. The resultant precipitates were collected by filtration and washed with ethanol. The filtrate and the washings were combined to prepare an ethanolic solution of O-cyclopentylhydroxylamine.

This solution was added to the aqueous solution prepared above, and the mixture was adjusted to pH 3 to 4 with 6 N hydrochloric acid, followed by stirring at ambient temperature for 1.5 hours. The reaction mixture was neutralized with an aqueous sodium bicarbonate and concentrated to half of the original volume under reduced pressure, followed by washing with ethyl acetate. The resultant aqueous solution was acidified with 6 N hydrochloric acid and then extracted with ethyl acetate. The extract was dried over magnesium sulfate and evaporated to dryness. The residue was triturated with diisopropyl ether to obtain 2-cyclopentyloxyimino-2-(4-formamidopyrimidin-2-yl)acetic acid (syn isomer) (0.99 g), mp 145°–147° C. (dec.).

IR (Nujol): 3100, 1740, 1680, 1570, 1530, 1440, 1000, 860, 800, 720, 660 cm$^{-1}$.

NMR(DMSO-d$_6$,δ): 1.4–2.1 (8H, m), 4.7–5.0 (1H, m), 7.2–7.8 (1H, m), 8.6–9.2 (1H, m), 8.70 (1H, d, J=6 Hz), 11.3 (1H, d, J=6 Hz).

PREPARATION 2

2-Cyclopentyloxyimino-2-(6-formamidopyridin-2-yl)acetic acid (syn isomer) (5.2 g), mp 138° to 146° C. (dec.) was obtained from S-methyl (6-formamidopyridin-2-yl)thioglyoxylate (6.72 g) and O-cyclopentylhydroxylamine, which was prepared from N-cyclopentyloxyphthalimide (6.94 g) and hydrazine monohydrate (1.43 g), by treating them according to a similar manner to that of Preparation 1.

IR (Nujol): 3230, 2500, 1725, 1650, 1608, 1575, 1300, 1265, 1250, 1240, 1160, 1010, 810 cm$^{-1}$.

NMR (DMSO-d$_6$,δ): 1.7 (8H, m), 4.87 (1H, m), 6.8–8.6 (3H, m), 9.20 (1H, broad s), 10.75 (1H, d, J=7 Hz).

PREPARATION 3

To a suspension of S-methyl (4-formamidopyrimidin-2-yl)thioglyoxylate (11.3 g) in water (120 ml) was added 1 N aqueous sodium hydroxide (45 ml), followed by stirring at ambient temperature for 20 minutes to produce a solution containing sodium (4-formamidopyrimidin-2-yl)glyoxylate.

On the other hand, a mixture of N-(2-cyclopenten-1-yloxy)phthalimide (13.7 g) and hydrazine monohydrate (2.85 g) in ethanol (70 ml) was refluxed under heating for 5 minutes and then cooled in an ice-bath. The resultant precipitates were collected by filtration and washed with ethanol. The filtrate and the washings were combined to prepare an ethanolic solution of O-(2-cyclopenten-1-yl)hydroxylamine.

This solution was added to the aqueous solution prepared above, and the mixture was adjusted to pH 3 to 4 with hydrochloric acid, followed by stirring at ambient temperature for 1.5 hours. The reaction mixture was neutralized with an aqueous sodium bicarbonate and concentrated to half of the original volume under reduced pressure, followed by washing with ethyl acetate. The resultant aqueous solution was acidified with 6 N hydrochloric acid and then extracted with ethyl acetate. The extract was dried over magnesium sulfate and evaporated to dryness. The residue was triturated with diisopropyl ether to obtain 2-(2-cyclopenten-1-yloxyimino)-2-(4-formamidopyrimidin-2-yl)acetic acid (syn isomer) (5.97 g), mp 141°–143° C. (dec.).

IR (Nujol): 3200, 3100, 2550, 2450, 1730, 1570, 1530, 1440, 1310, 1250, 1000, 985, 870, 850, 670 cm$^{-1}$.

NMR (DMSO-d$_6$,δ): 1.5–2.5 (4H, m), 5.2–5.7 (1H, m), 5.8–6.1 (1H, m), 6.1–6.4 (1H, m), 7.1–8.0 (1H, m), 7.33 (1H, d, J=6 Hz), 8.7–9.2 (1H, m), 11.2 (1H, d, J=6 Hz).

PREPARATION 4

2-(2-Cyclopenten-1-yloxyimino)-2-(6-formamidopyridin-2-yl)acetic acid (syn isomer) (4.8 g), mp 143° to 147° C. (dec.), was obtained from S-methyl (6-formamidopyridin-2-yl)thioglyoxylate (6.72 g) and O-(2-cyclopenten-1-yl)hydroxylamine, which was prepared from N-(2-cyclopenten-1-yloxy)phthalimide (6.88 g) and hydrazine monohydrate (1.43 g), by treating them according to a similar manner to that of Preparation 3.

IR (Nujol): 3280, 2500, 1725, 1655, 1608, 1570, 1300, 1265, 1240, 1200, 1160, 1000, 810, 740 cm$^{-1}$.

NMR (DMSO-d$_6$,δ): 1.5–2.8 (4H, m), 5.1–5.7 (1H, m), 5.8–6.3 (2H, m), 6.7–8.7 (3H, m), 9.3 (1H, broad s), 10.70 (1H, d, J=7 Hz).

PREPARATION 5

1 N Aqueous sodium hydroxide (49 ml) was added to a suspension of S-methyl (6-formamidopyridin-2-yl)thioglyoxylate (10 g) in methanol (100 ml), and the mixture was stirred at ambient temperature for 50 minutes to prepare the solution of sodium (6-formamidopyridin-2-yl)glyoxylate. To this solution was added tert-butyl 2-aminooxyacetate (7.2 g) and the mixture was adjusted to pH 3 to 4 with 6 N hydrochloric acid, followed by stirring at ambient temperature for 4 hours. The reaction mixture was neutralized with an aqueous sodium bicarbonate and concentrated to half of the original volume under reduced pressure, followed by washing with ethyl acetate and adjusting to pH 1.5 with 10% hydrochloric acid.

The resultant aqueous solution was extracted three times with ethyl acetate, and the combined extracts were washed with a saturated aqueous sodium chloride and dried over magnesium sulfate. Removal of the solvent gave 2-tert-butoxycarbonylmethoxyimino-2-(6-formamidopyridin-2-yl)acetic acid (syn isomer) (11.9 g), mp 162°–168° C.

IR (Nujol): 3180, 1741, 1673 cm$^{-1}$.

NMR δppm (DMSO-d$_6$): 1.47 (9H, s), 4.73 (2H, s), 7.3–8.3 (3H, m), 9.17 (1H, broad s), 10.7 (1H, d, J=6 Hz).

PREPARATION 6

To a suspension of S-methyl (4-formamidopyrimidin-2-yl)thioglyoxylate (5.0 g) in water (45 ml) was added 1 N aqueous solution of sodium hydroxide (21 ml) and the mixture was stirred for 30 minutes at room temperature to produce a solution containing sodium (4-formamidopyrimidin-2-yl)glyoxylate. On the other hand, a mixture of N-methylthiomethoxyphthalimide (5.0 g) and hydrazine hydrate (1.0 g) in ethanol (25 ml) was refluxed for 5 minutes and then cooled in an ice-bath. A resulting precipitate was filtered off and washed with ethanol. The filtrate and the washings were conbined to prepare an ethanolic solution of O-methylthiomethylhydroxylamine.

This solution was added to the above aqueous solution. The mixture was adjusted to pH 4 with 1 N hydrochloric acid and stirred for one hour at room temperature. The solution was neutralized with an aqueous solution of sodium bicarbonate, concentrated to half volume in vacuo, adjusted to pH 4 with 1 N hydrochloric acid and washed with ethyl acetate. The aqueous solution was adjusted to pH 1 with 1 N hydrochloric acid, saturated with sodium chloride and extracted with ethyl acetate. The extract was dried over magnesium sulfate and evaporated to dryness. The residue was triturated in n-hexane to give 2-methylthiomethoxyimino-2-(4-formamidopyrimidin-2-yl)acetic acid (syn isomer) (3.25 g), mp 80° to 85° C.

IR (Nujol): 3450, 3200, 1710, 1620, 1565, 1510 cm$^{-1}$.

NMR (DMSO-d$_6$, δ): 2.23 (3H, s), 5.40 (2H, s), 7.3–7.8 (1H, m), 8.72 (1H, d, J=6 Hz), 8.8–9.1 (1H, m), 11.22 (1H, d, J=6 Hz).

PREPARATION 7

2-Propargyloxyimino-2-(4-formamidopyrimidin-2-yl)acetic acid (syn isomer) was obtained from S-methyl (4-formamidopyrimidin-2-yl)thioglyoxylate and O-propargylhydroxylamine hydrochloride by treating them according to a similar manner to that of Preparation 6.

mp 78° to 83° C. (dec.).

IR (Nujol): 3250, 1710, 1570, 1210, 1010 cm$^{-1}$.

NMR (DMSO-d$_6$+D$_2$O, δ): 3.63 (1H, t, J=2 Hz), 4.90 (2H, d, J=2 Hz), 7.3–7.7 (1H, m), 8.65 (1H, d, J=8 Hz), 8.7–9.1 (1H, m).

PREPARATION 8

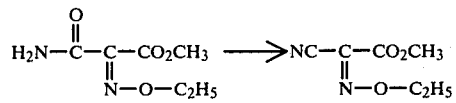

To a solution of methyl 2-carbamoyl-2-ethoxyiminoacetate (syn isomer) (5.22 g) in pyridine (50 ml) was dropwise added trifluoroacetic anhydride (15.7 g) below 25° C. under cooling in an ice-bath and stirring, which was continued for 30 minutes. The reaction mixture was poured into water (200 ml), followed by an addition of diisopropyl ether (200 ml). The mixture was adjusted to pH 2 with 6 N hydrochloric acid (80 ml) at 15° to 20° C. and the organic layer was separated out, washed with water, dried over magnesium sulfate and evaporated to give methyl 2-cyano-2-ethoxyiminoacetate (syn isomer) (4.23 g) as an oil.

IR (film): 2250, 1760, 1557, 1440, 1270, 1050 cm$^{-1}$.

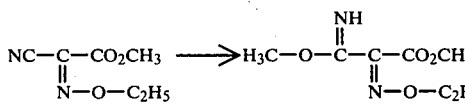

To a solution of methyl 2-cyano-2-ethoxyiminoacetate (syn isomer) (4.7 g) in methanol (50 ml) was added 1 N methanolic solution (5 ml) of sodium methoxide under cooling in an ice-bath and stirring, which was continued for 20 minutes in an ice-bath and 15 minutes at room temperature. The mixture was neutralized to the end point of phenolphthalein with 1 N methanolic solution of acetic acid and evaporated. The residue was dissolved in methylene chloride (80 ml), washed with water, dried over magnesium sulfate and evaporated to give methyl 3-imino-3-methoxy-2-ethoxyiminopropionate (syn isomer) (4.8 g) as an oil.

IR (film): 3340, 1755, 1665, 1645, 1610 cm$^{-1}$.

NMR (CDCl$_3$, δ): 1.32 (3H, t, J=7 Hz), 3.84 (3H, s), 3.87 (3H, s), 4.28 (2H, q, J=7 Hz), 8.25 (1H, broad s).

PREPARATION 9

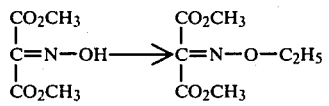

To a mixture of dimethyl isonitrosomalonate (12.25 g) and diethyl sulfate (14.32 g) in N,N-dimethylformamide (12 ml) was dropped triethylamine (9.39 g) at 30° to 40° C. under stirring, which was continued for 1.5 hours at the same temperature. The mixture was diluted with methylene chloride (45 ml) and water (30 ml), and then the organic layer was separated out, washed with 5% aqueous potassium carbonate and water, dried over magnesium sulfate and evaporated to give an oily residue (11.5 g). The residue was distilled under reduced pressure (5 mmHg) to give dimethyl ethoxyiminomalonate (5.5 g), bp. 85° to 105° C. (5 mmHg).

IR (Film): 3000, 2970, 1755, 1730, 1610 cm$^{-1}$.

NMR (CDCl$_3$, δ): 1.30 (3H, t, J=7), 3.83 (6H, s), 4.32 (2H, q, J=7 Hz).

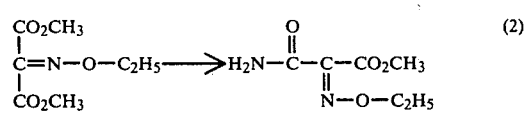

A mixture of dimethyl ethoxyiminomalonate (57.4 g) and conc. ammonium hydroxide (50 ml) in methanol (150 ml) was stirred for 2.5 hours at room temperature. The mixture was adjusted to pH 4 with conc. hydrochloric acid under cooling and concentrated to 70 ml under reduced pressure. The aqueous solution was stood in a refrigerator for one hour and the resulting precipitates were collected by filtration, washed with cold water and dried to give methyl 2-carbamoyl-2-ethoxyiminoacetate (syn isomer) (31 g), mp 68° to 71° C.

IR (Nujol): 3450, 3300, 3200, 1740, 1680, 1660, 1600 cm$^{-1}$.

NMR (DMSO-d$_6$, δ): 1.28 (3H, t, J=7 Hz), 3.83 (3H, s), 4.28 (2H, q, J=7 Hz), 7.70 (2H, broad s).

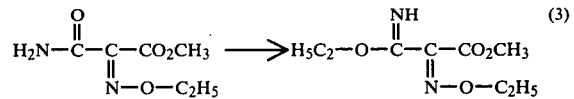

To a solution of Meerwein reagent (triethyloxonium tetrafluoroborate) {prepared from bron fluoride etherate (2.84 g) by a method of Org. Syn., 46, 113 (1966)} in methylene chloride (30 ml) was added methyl 2-carbamoyl-2-ethoxyiminoacetate (syn isomer, 2.6 g) and the mixture was stirred for 18 hours at room temperature. The reaction mixture was cooled in an ice-bath and triethylamine (3 g) was added thereto, followed by an addition of water (20 ml). The organic layer was separated out, dried over magnesium sulfate and evaporated to give crude methyl 3-imino-3-ethoxy-2-ethoxyiminopropionate (syn isomer) (5.0 g) as an oil.

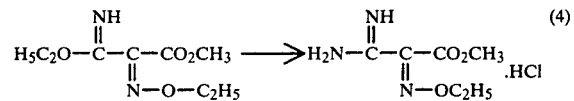

A solution of the above obtained crude methyl 3-imino-3-ethoxy-2-ethoxyiminopropionate (syn isomer) (5.0 g) and ammonium chloride (802 mg) in methanol (25 ml) was stirred for 6 hours at room temperature and evaporated to dryness to give a residue.

The residue was triturated with ethyl acetate to give methyl 2-amidino-2-ethoxyiminoacetate hydrochloride (syn isomer) (1.75 g), mp. 138° to 140° C. (dec.).

IR (Nujol): 2600, 2490, 1740, 1680, 1595 cm$^{-1}$.

NMR (DMSO-d$_6$, δ): 1.33 (3H, t, J=7 Hz), 3.90 (3H, s), 4.45 (2H, q, J=7 Hz).

(5) A mixture of methyl 2-amidino-2-ethoxyiminoacetate hydrochloride (syn isomer) (2.1 g), 2-chloroacrylonitrile (875 mg) and triethylamine (2.0 g) in ethanol (21 ml) was stirred for 8 hours at ambient temperature and allowed to stand at the same temperature overnight. The mixture was evaporated to dryness and the residue was dissolved in a mixture of ethyl acetate (20 ml) and water (10 ml). The organic layer was separated out, treated with activated charcoal and evaporated to dryness. The residue was purified by a column chromatography on silica gel (30 g) using ethyl acetate-benzene (1:1) as an eluant to give a mixture (1.0 g) of methyl 2-ethoxyimino-2-(4-aminopyrimidin-2-yl)acetate (syn isomer) and ethyl 2-ethoxyimino-2-(4-aminopyrimidin-2-yl)acetate (syn isomer) (1:1). mp 105° to 110° C.

IR (Nujol): 3500, 3390, 3350, 3100, 1745, 1635, 1580 cm$^{-1}$.

(6) A mixture (930 mg) of methyl 2-ethoxyimino-2-(4-aminopyrimidin-2-yl)acetate (syn isomer) and ethyl 2-ethoxyimino-2-(4-aminopyrimidin-2-yl)acetate (syn isomer) in 1 N aqueous sodium hydroxide (4.95 ml) was stirred for 3.5 hours at ambient temperature. The solution was passed through an ion exchange resin [16 ml, Amberlite IRC-50 (trademark: Prepared by Rohm and Haas Co.)] and evaporated to dryness. The residue was triturated in a mixed solvent of acetone (20 ml) and water (2 ml) to give 2-ethoxyimino-2-(4-aminopyrimidin-2-yl)acetic acid (syn isomer) (0.8 g), mp. 180° to 182° C. (dec.).

IR (Nujol): 3560, 3400, 3250, 1640, 1605, 1530 cm$^{-1}$.

NMR (D$_2$O, δ): 1.33 (3H, t, J=7 Hz), 4.33 (2H, q, J=7 Hz), 6.67 (1H, d, J=7 Hz), 8.05 (1H, d, J=7 Hz).

PREPARATION 10

A mixture of phosphorus oxychloride (5.0 g) and N,N-dimethylformamide (2.39 g) was stirred for 30 minutes at 40° to 50° C. and methylene chloride (110 ml) was added thereto. The mixture was cooled to −20° C. and 2-propargyloxyimino-2-(4-formamidopyrimidin-2-yl)acetic acid (syn isomer) (4.45 g) was added thereto. The mixture was stirred for 50 minutes at −17° to −10° C. to give an activated acid solution. On the other hand, a mixture of 7-aminocephalosporanic acid (5.25 g) and trimethylsilylacetamide (27 g) in methylene chloride (110 ml) was stirred at room temperature to make a solution, which was cooled to −20° C. To the cold solution was added the above activated acid solution and the mixture was stirred for one hour at −15° to −10° C. The reaction mixture was poured into an aqueous solution (150 ml) of sodium bicarbonate (13.7 g) and the aqueous layer was separated out. The aqueous solution was washed with ethyl acetate, adjusted to pH 2 to 3 with 6 N hydrochloric acid and extracted with ethyl acetate. The extract was treated with activated charcoal, evaporated to dryness and triturated in diethyl ether to give 7-[2-propargyloxyimino-2-(4-formamidopyrimidin-2-yl)acetamido]cephalosporanic acid (syn isomer) (4.37 g), mp. 165° to 173° C. (dec.).

IR (Nujol): 3250, 1780, 1710, 1670, 1570, 1235, 1220, 1040, 1020 cm$^{-1}$.

NMR (DMSO-d$_6$, δ): 2.04 (3H, s), 2H, m) 3.53 (1H, t, J=2 Hz), 4.63 and 4.95 (2H, ABq, J=14 Hz), 4.88 (2H, d, J=2 Hz), 5.17 (1H, d, J=5 Hz), 5.85 (1H, dd, J=5 and 8 Hz), 7.1-7.7 (1H, m), 8.65 (1H, d, J=5 Hz), 8.8-9.3 (1H, m), 9.53 (1H, d, J=8 Hz), 11.2 (1H, m).

PREPARATION 11

7-[2-Ethoxyimino-2-(4-aminopyrimidin-2-yl)acetamido]cephalosporanic acid (syn isomer) (14.98 g) was obtained from 7-aminocephalosporanic acid (12.86 g) and 2-ethoxyimino-2-(4-aminopyrimidin-2-yl)acetic acid (syn isomer) (9.3 g) by treating them according to a similar manner to that of Preparation 10.

mp 182° to 186° C. (dec.)

IR (Nujol): 3400, 3250, 1770, 1740, 1670, 1650, 1600, 1540 cm$^{-1}$.

NMR (DMSO-d$_6$, δ): 1.27 (3H, t, J=7 Hz), 2.02 (3H, s), 3.53 (2H, m), 4.23 (2H, q, J=7 Hz), 4.67 and 5.02 (2H, ABq, J=14 Hz), 5.17 (1H, d, J=5 Hz), 5.82 (1H, dd, J=5 and 8 Hz), 6.42 (1H, d, J=6 Hz), 6.97 (2H, broad s), 8.10 (1H, d, J=6 Hz), 9.35 (1H, d, J=8 Hz).

PREPARATION OF THE OBJECT COMPOUNDS

Example 1

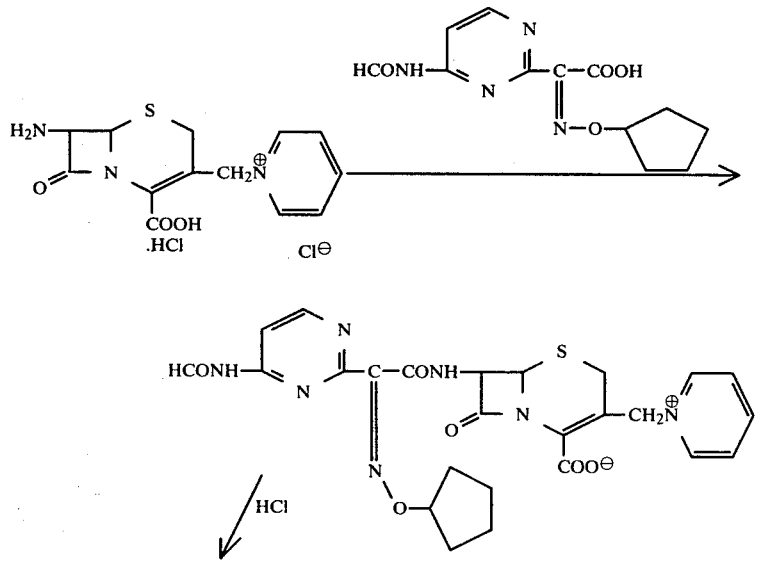

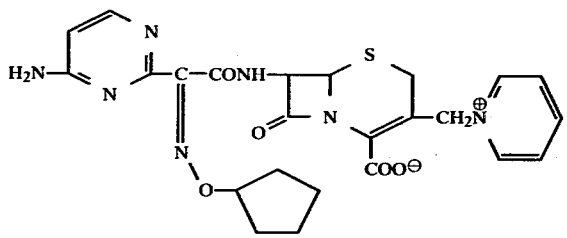

A mixture of N,N-dimethylformamide (2.6 ml) and phosphorus oxychloride (2.58 g) was warmed for half an hour. After cooling, methylene chloride (36 ml) was added thereto. 2-Cyclopentyloxyimino-2-(4-formamidopyrimidin-2-yl)acetic acid (syn isomer) (3.34 g) was added thereto at −25° C., and the mixture was stirred at −20° to −15° C. for half an hour to prepare the activated acid solution.

On the other hand, a mixture of 1-[(7-amino-4-carboxy-3-cephem-3-yl)methyl]pyridinium chloride monohydrochloride [which can also be named as 7-amino-3-(1-pyridiniomethyl)-3-cephem-4-carboxylate dihydrochloride] (3.64 g) and trimethylsilylacetamide (20.0 g) in methylene chloride (36 ml) was stirred at ambient temperature for 20 minutes, followed by cooling to −15° C.

This solution was added to the activated acid solution prepared above, and the mixture was stirred at −20° to −12° C. for 45 minutes and at ambient temperature for additional an hour. The reaction mixture was poured into an aqueous solution (100 ml) of sodium bicarbonate (8.47 g). The aqueous layer containing 7-[2-cyclopentyloxyimino-2-(4-formamidopyrimidin-2-yl)acetamido]-3-(1-pyridiniomethyl)-3-cephem-4-carboxylate (syn isomer) was separated out, adjusted to pH 1 with 6 N hydrochloric acid and washed with ethyl acetate, followed by standing at 5° C. for 15 hours. This aqueous solution was subjected to column chromatography on a non-ionic adsorption resin "Diaion HP-20" (Trade mark, manufactured by Mitsubishi Chemical Industries) (100 ml). After the column was washed with water, elution was carried out with 7.5% aqueous isopropyl alcohol. The eluates containing a desired compound were collected, evaporated to remove isopropyl alcohol under reduced pressure. The resultant solution was lyophilized to give pale-yellow powder of 7-[2-cyclopentyloxyimino-2-(4-aminopyrimidin-2-yl)acetamido]-3-(1-pyridiniomethyl)-3-cephem-4-carboxylate (syn isomer) (1.67 g), mp 165°–180° C. (dec.).

IR (Nujol): 3300, 3200, 1770, 1670, 1620, 1580, 1340, 990, 770, 680 cm$^{-1}$.

NMR (D$_2$O,δ): 1.2–2.0 (8H, m), 3.03, 3.60 (2H, ABq, J=18 Hz), 4.8 (1H, m), 5.08 (1H, d, J=5 Hz), 5.70 (1H, d, J=5 Hz), 5.1–5.9 (2H, m), 6.47 (1H, d, J=6 Hz), 8.10 (1H, d, J=6 Hz), 8.2 (2H, m), 8.6 (1H, m), 9.4 (2H, m).

EXAMPLE 2

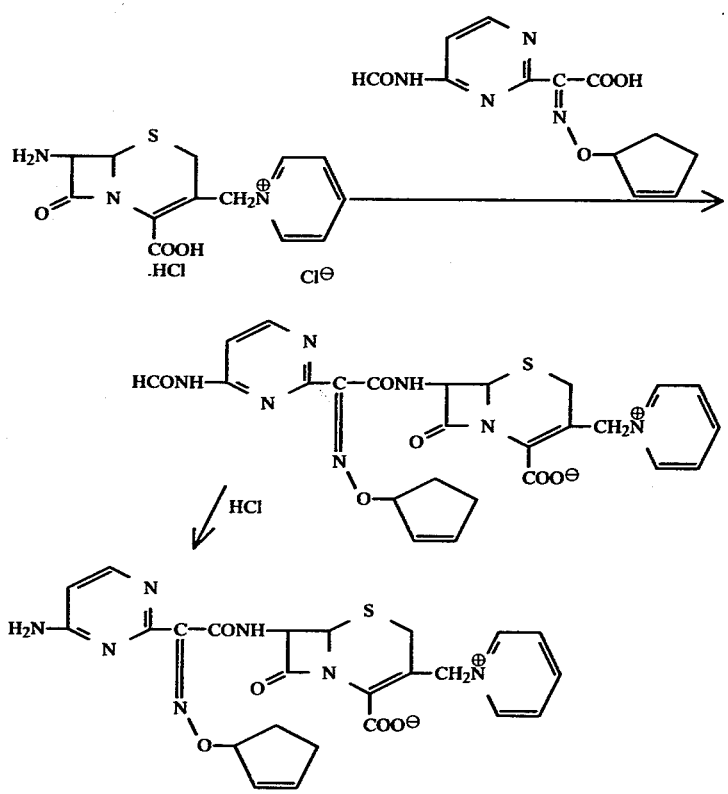

A mixture of N,N-dimethylformamide (2.6 ml) and phosphorus oxychloride (2.58 g) was warmed for half an hour. After cooling, methylene chloride (36 ml) was added thereto. 2-(2-Cyclopenten-1-yloxyimino)-2-(4-formamidopyrimidin-2-yl)acetic acid (syn isomer) (3.31 g) was added at −25° C., and the mixture was stirred at −20° to −13° C. for half an hour to prepare the activated acid solution.

On the other hand, a mixture of 1-[(7-amino-4-carboxy-3-cephem-3-yl)methyl]pyridinium chloride monohydrochloride (3.64 g) and trimethylsilylacetamide (20.0 g) in methylene chloride (36 ml) was stirred at ambient temperature for 20 minutes, followed by cooling to −20° C.

This solution was added to the activated acid solution prepared above, and the mixture was stirred at −19° to −10° C. for half an hour and at ambient temperature for additional half an hour. The reaction mixture was poured into an aqueous solution (100 ml) of sodium bicarbonate (8.47 g). The aqueous layer containing 7-[2-(2-cyclopenten-1-yloxyimino)-2-(4-formamidopyrimidin-2-yl)acetamido]-3-(1-pyridiniomethyl)-3-cephem-4-carboxylate (syn isomer) was separated out, adjusted to pH 1 with 6 N hydrochloric acid and washed with ethyl acetate, followed by standing at 5° C. for 15 hours. This aqueous solution was subjected to column chromatography on a non-ionic adsorption resin "Diaion HP-20" (200 ml). After the column was washed with water, elution was carried out with 10% aqueous isopropyl alcohol. The eluates containing a desired compound were collected, evaporated to remove isopropyl alcohol under reduced pressure. The resultant solution was lyophilized to give yellowish white powder of 7-[2-(2-cyclopenten-1-yloxyimino)-2-(4-aminopyrimidin-2-yl)acetamido]-3-(1-pyridiniomethyl)-3-cephem-4-carboxylate (syn isomer) (1.97 g), mp 160°–175° C. (dec.).

IR (Nujol): 3300, 3200, 1770, 1660, 1620, 1580, 1540, 1360, 1150, 1100, 980, 770, 680 cm$^{-1}$.

NMR (D$_2$O+δ): 1.5–2.5 (4H, m), 3.10, 3.63 (2H, ABq, J=18 Hz), 5.13 (1H, d, J=5 Hz), 5.2–6.3 (5H, m), 5.80 (1H, d, J=5 Hz), 6.53 (1H, d, J=6 Hz), 8.17 (1H, d, J=6 Hz), 8.2 (2H, m), 8.6 (1H, m), 9.3 (2H, m).

EXAMPLE 3

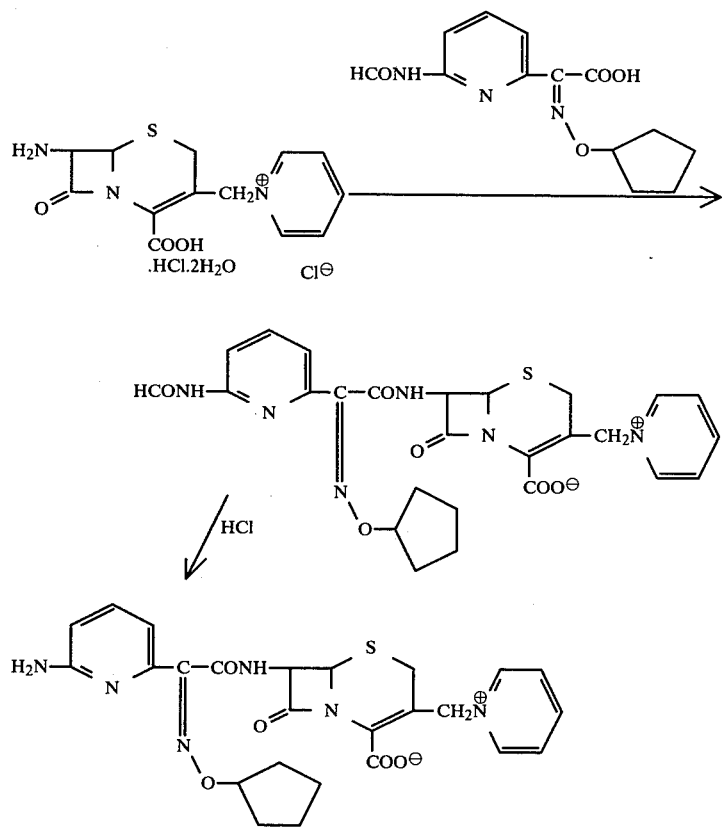

7-[2-Cyclopentyloxyimino-2-(6-aminopyridin-2-yl)acetamido]-3-(1-pyridiniomethyl)-3-cephem-4-carboxylate (syn isomer) (1.5 g), mp 137° to 145° C. (dec.), was obtained by reacting 1-[(7-amino-4-carboxy-3-cephem-3-yl)methyl]pyridinium chloride monohydrochloride dihydrate (3.0 g) with 2-cyclopentyloxyimino-2-(6-formamidopyridin-2-yl)acetic acid (syn isomer) (2.50 g), and then reacting the resultant 7-[2-cyclopentyloxyimino-2-(6-formamidopyridin-2-yl)acetamido]-3-(1-pyridiniomethyl)-3-cephem-4-carboxylate (syn isomer) with 6 N hydrochloric acid, according to a similar manner to those of Examples 1 and 2.

IR (Nujol): 3330, 3180, 1775, 1660, 1610 cm$^{-1}$

NMR (DMSO-d$_6$+D$_2$O,δ): 1.7 (8H, m), 3.13, 3.62 (2H, ABq, J=18 Hz), 4.80 (1H, broad s), 5.18 (1H, d, J=5 Hz), 5.2–5.8 (2H, m), 5.83 (1H, d, J=5 Hz), 6.60 (1H, d, J=8.5 Hz), 6.93 (1H, d, J=7 Hz), 7.51 (1H, dd, J=7 Hz, 8.5 Hz), 7.9–8.3 (2H, m), 8.3–8.8 (1H, m), 9.23 (2H, m).

EXAMPLE 4

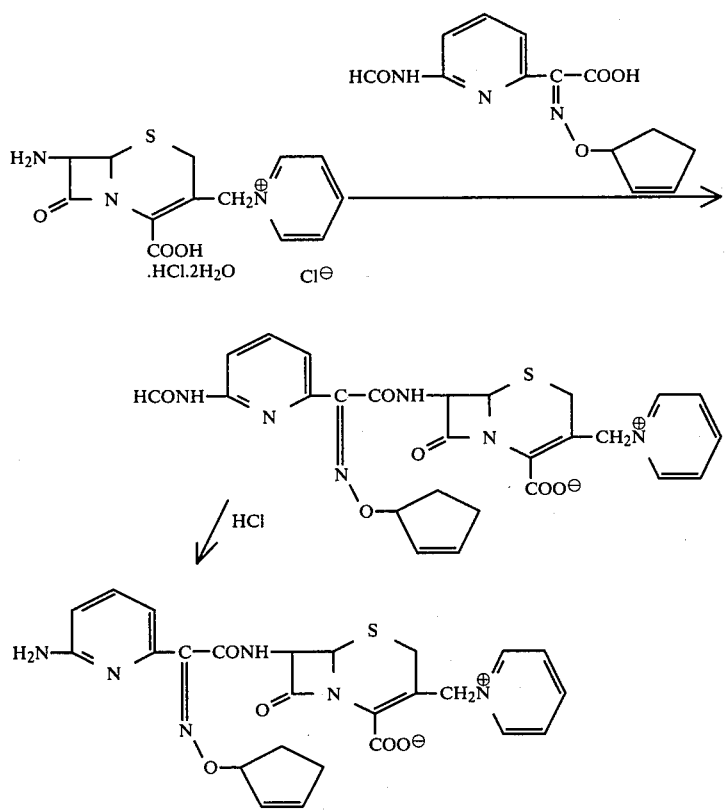

7-[2-(2-Cyclopenten-1-yloxyimino)-2-(6-aminopyridin-2-yl)acetamido]-3-(1-pyridiniomethyl)-3-cephem-4-carboxylate (syn isomer) (2.0 g), mp 139° to 145° C. (dec.), was obtained by reacting 1-[(7-amino-4-carboxy-3-cephem-3-yl)methyl]pyridinium chloride monohydrochloride dihydrate (3.0 g) with 2-(2-cyclopenten-1-yloxyimino)-2-(6-formamidopyridin-2-yl)acetic acid (syn isomer) (2.5 g), and then reacting the resultant 7-[2-(2-cyclopenten-1-yloxyimino)-2-(6-formamidopyridin-2-yl)acetamido]-3-(1-pyridiniomethyl)-3-cephem-4-carboxylate (syn isomer) with 6 N hydrochloric acid, according to a similar manner to those of Examples 1 and 2.

IR (Nujol): 3330, 3180, 1770, 1660, 1610 cm$^{-1}$.

NMR (DMSO-d$_6$+D$_2$O,δ): 1.7–2.6 (4H, m), 3.17, 3.67 (2H, ABq, J=18 Hz), 5.18 (1H, d, J=5 Hz), 5.82 (1H, d, J=5 Hz), 5.0–5.7 (3H, m), 5.9–6.3 (2H, m), 6.62 (1H, d, J=8.5 Hz), 6.97 (1H, d, J=7.8 Hz), 7.56 (1H, dd, J=7.8 Hz, 8.5 Hz), 7.9–8.4 (2H, m), 8.4–8.8 (1H, m), 9.21 (2H, m).

EXAMPLE 5

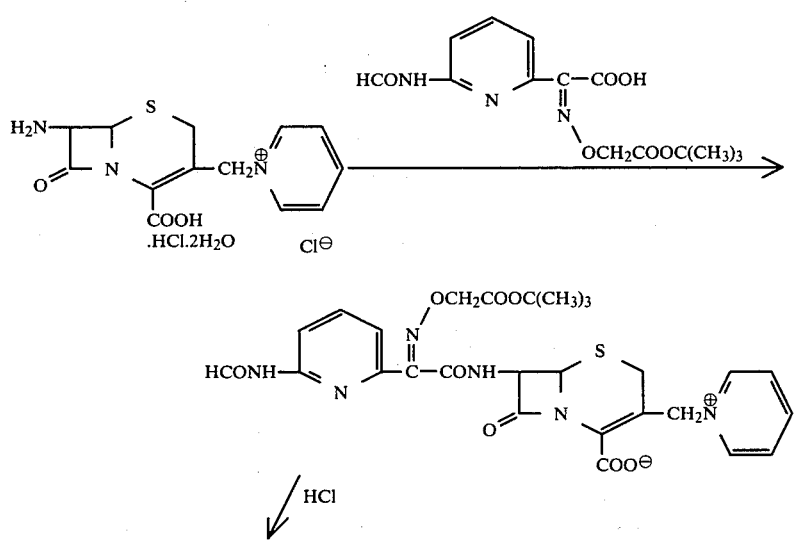

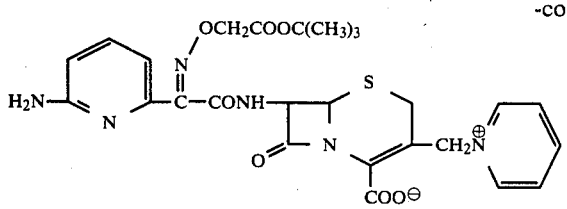

7-[2-tert-Butoxycarbonylmethoxyimino-2-(6-aminopyridin-2-yl)-acetamido]-3-(1-pyridiniomethyl)-3-cephem-4-carboxylate (syn isomer) (4.0 g), mp 94° to 104° C. (dec.), was obtained by reacting 1-[(7-amino-4-carboxy-3-cephem-3-yl)methyl]pyridinium chloride monohydrochloride dihydrate (4.8 g) with 2-tert-butoxycarbonylmethoxyimino-2-(6-formamidopyridin-2-yl)acetic acid (syn isomer) (4.26 g), and then reacting the resultant 7-[2-tert-butoxycabonylmethoxyimino-2-(6-formamidopyridin-2-yl)acetamido]-3-(1-pyridiniomethyl)-3-cephem-4-carboxylate (syn isomer) with 6 N hydrochloric acid, according to a similar manner to those of Examples 1 and 2.

IR (Nujol): 3340, 1770, 1670, 1610 cm$^{-1}$.

NMR (DMSO-d$_6$+D$_2$O, δ): 1.43 (9H, s), 3.13, 3.58 (2H, ABq, J=17 Hz), 4.65 (2H, s), 5.15 (1H, d, J=5 Hz), 5.1–5.8 (2H, m), 5.83 (1H, d, J=5 Hz), 6.60 (1H, d, J=8 Hz), 6.90 (1H, d, J=7 Hz), 7.50 (1H, dd, J=7 Hz, 8 Hz), 7.8–8.2 (2H, m), 8.3–8.8 (1H, m), 9.16 (2H, m).

EXAMPLE 6

7-[2-Propargyloxyimino-2-(4-aminopyrimidin-2-yl)acetamido]-3-(1-pyridiniomethyl)-3-cephem-4-carboxylate (syn isomer) was obtained by reacting 1-[(7-amino-4-carboxy-3-cephem-3-yl)methyl]pyridinium chloride monohydrochloride dihydrate with 2-propargyloxyimino-2-(4-formamidopyrimidin-2-yl)acetic acid (syn isomer) according to similar manners to those of Examples 1 and 2.

mp 158° to 162° C. (dec.).

IR (Nujol): 3400–3150, 1770, 1670–1580, 1000 cm$^{-1}$.

NMR (D$_2$O, δ): 3.00 (1H, t, J=2 Hz), 3.15 and 3.68 (2H, ABq, J=18 Hz), 4.88 (2H, d, J=2 Hz), 5.25 (1H, d, J=5 Hz), 5.30 and 5.62 (2H, ABq, J=14 Hz), 5.87 (1H, d, J=5 Hz), 6.55 (1H, d, J=6 Hz), 7.9–8.2 (3H, m), 8.3–8.7 (1H, m), 8.8–9.0 (2H, m).

EXAMPLE 7

7-[2-t-Butoxycarbonylmethoxyimino-2-(4-aminopyrimidin-2-yl)acetamido]-3-(1-pyridiniomethyl)-3-cephem-4-carboxylate (syn isomer) was obtained by reacting 1-[(7-amino-4-carboxy-3-cephem-3-yl)methyl]pyridinium chloride monohydrochloride dihydrate with 2-t-butoxycarbonylmethoxyimino-2-(4-formamidopyrimidin-2-yl)acetic acid (syn isomer) according to similar manners to those of Examples 1 and 2.

mp 155° to 160° C. (dec.).

IR (Nujol): 3350, 3200, 1775, 1630, 1590, 1245, 1155 cm$^{-1}$.

NMR (DMSO-d$_6$, δ): 1.42 (9H s), 3.05 and 3.62 (2H, ABq, J=18 Hz), 4.60 (2H, broad s), 5.10 (1H, d, J=5 Hz), 5.17 and 5.72 (2H, ABq, J=14 Hz), 5.73 (1H, dd, J=5 and 8 Hz), 6.33 (1H, d, J=6 Hz), 7.0 (2H, broad s) 8.06 (1H, d, J=6 Hz), 8.0–8.3 (1H, m), 8.4–8.7 (1H, m), 9.25 (1H, d, J=8 Hz), 9.3–9.6 (2H, m).

EXAMPLE 8

To a suspension of 2-ethoxyimino-2-(4-aminopyrimidin-2-yl)acetic acid (syn isomer) (750 mg) in methylene chloride (10 ml) was dropped a solution of phosphorus oxychloride (1.64 g) in methylene chloride (5 ml) at 0° to 5° C. under stirring, which was continued for 30 minutes. The mixture was cooled to −16° C. and N,N-dimethylformamide (3 ml) was dropped thereto under stirring, which was continued for 30 minutes at −10° C.

On the other hand, a mixture of 1-[(7-amino-4-carboxy-3-cephem-3-yl)methyl]pyridinium chloride monohydrochloride dihydrate (1.43 g) and trimethylsilylacetamide (7 g) in methylene chloride (35 ml) was warmed to make a solution and then cooled to −15° C. To the cold solution was added the above obtained solution and the mixture was stirred for 30 minutes at −10° C. To the reaction mixture was added 5% aqueous solution of sodium bicarbonate and the mixture was stirred for 30 minutes at room temperature. The aqueous layer was separated out, adjusted to pH 2 with 6 N hydrochloric acid and washed with ethyl acetate. The aqueous solution was subjected to column chromatography on a non ionic adsorption resin "Diaion Hp-20" (100 ml). After the column was washed with water, the elution was carried out with 30% aqueous methanol. The eluate (300 ml) was evaporated to remove methanol under reduced pressure and lyophilized to give 7-[2-ethoxyimino-2-(4-aminopyrimidin-2-yl)acetamido]-3-(1-pyridiniomethyl)-3-cephem-4-carboxylate (syn isomer) (1.07 g), mp. 155° to 160° C. (dec.).

IR (Nujol): 3320, 3190, 1770, 1660, 1610, 1580, 1540 cm$^{-1}$.

NMR (DMSO-d$_6$, δ): 1.20 (3H, t, J=7 Hz), 3.08 and 3.47 (2H, ABq, J=17 Hz), 4.13 (2H, q, J=7 Hz), 5.03 (1H, d, J=5 Hz), 5.20 and 5.63 (2H, ABq, J=14 Hz), 5.67 (1H, dd, J=5 and 8 Hz), 6.38 (1H, d, J=6 Hz), 6.97 (2H, broad s), 8.02 (1H, d, J=6 Hz), 7.93–8.30 (2H, m), 8.33–8.70 (1H, m), 9.23 (1H, d, J=8 Hz), 9.27–9.53 (2H, m).

EXAMPLE 9

The following compounds were obtained according to a similar manner to that of Example 8.

(1) 7-[2-Cyclopentyloxyimino-2-(4-aminopyrimidin-2-yl)acetamido]-3-(1-pyridiniomethyl)-3-cephem-4-carboxylate (syn isomer).

mp 165° to 180° C. (dec.).

IR (Nujol): 3300, 3200, 1770, 1670, 1620, 1580, 1340, 990, 770, 680 cm$^{-1}$.

(2) 7-[2-(2-Cyclopenten-1-yloxyimino)-2-(4-aminopyrimidin-2-yl)acetamido]-3-(1-pyridiniomethyl)-3-cephem-4-carboxylate (syn isomer).

mp 160° to 175° C. (dec.).

IR (Nujol): 3300, 3200, 1770, 1660, 1620, 1580, 1540, 1360, 1150, 1100, 980, 770, 680 cm$^{-1}$.

(3) 7-[2-Cyclopentyloxyimino-2-(6-aminopyridin-2-yl)acetamido]-3-(1-pyridiniomethyl)-3-cephem-4-carboxylate (syn isomer).

mp 137° to 145° C. (dec.).

IR (Nujol): 3330, 3180, 1775, 1660, 1610 cm$^{-1}$.

(4) 7-[2-(2-Cyclopenten-1-yloxyimino)-2-(6-aminopyridin-2-yl)acetamido]-3-(1-pyridiniomethyl)-3-cephem-4-carboxylate (syn isomer).
mp 139° to 145° C. (dec.).
IR (Nujol): 3330, 3180, 1770, 1660, 1610 cm$^{-1}$.

(5) 7-[2-tert-Butoxycarbonylmethoxyimino-2-(6-aminopyridin-2-yl)acetamido]-3-(1-pyridiniomethyl)-3-cephem-4-carboxylate (syn isomer).
mp 94° to 104° C. (dec.).
IR (Nujol): 3340, 1770, 1670, 1610 cm$^{-1}$.

(6) 7-[2-Carboxymethoxyimino-2-(6-aminopyridin-2-yl)acetamido]-3-(1-pyridiniomethyl)-3-cephem-4-carboxylate (syn isomer).
mp 100° to 108° C. (dec.).
IR (Nujol): 3340, 3180, 1775, 1645, 1610 cm$^{-1}$.

(7) 7-[2-Methylthiomethoxyimino-2-(4-formamidopyrimidin-2-yl)acetamido]-3-(1-pyridiniomethyl)-3-cephem-4-carboxylate (syn isomer).
mp 150° to 155° C. (dec.).
IR (Nujol): 3200, 1775, 1680, 1605, 1565, 1480 cm$^{-1}$.
NMR (D$_2$O,δ): 2.25 (3H, s), 3.30 and 3.67 (2H, ABq, J=18 Hz), 5.33 (1H, d, J=5 Hz), 5.42 (2H, s), 5.42 and 5.62 (2H, ABq, J=14 Hz), 5.97 (1H, d, J=5 Hz), 7.17–7.60 (1H, m), 8.0–8.35 (2H, m), 8.47–8.82 (2H, m), 8.90–9.37 (3H, m).

(8) 7-[2-Propargyloxyimino-2-(4-aminopyrimidin-2-yl)acetamido]-3-(1-pyridiniomethyl)-3-cephem-4-carboxylate (syn isomer).
mp 158° to 162° C. (dec.).
IR (Nujol): 3400–3150, 1770, 1670–1580, 1000 cm$^{-1}$.

(9) 7-[2-t-Butoxycarbonylmethoxyimino-2-(4-aminopyrimidin-2-yl)acetamido]-3-(1-pyridiniomethyl)-3-cephem-4-carboxylate (syn isomer).
mp 155° to 160° C. (dec.).
IR (Nujol): 3350, 3200, 1775, 1630, 1590, 1245, 1155 cm$^{-1}$.

(10) 7-[2-Carboxymethoxyimino-2-(4-aminopyrimidin-2-yl)acetamido]-3-(1-pyridiniomethyl)-3-cephem-4-carboxylate (syn isomer).
mp 105° to 110° C. (dec.).
IR (Nujol): 3350, 3200, 1770, 1680–1570, 1200 cm$^{-1}$.

(11) 7-[2-Methylthiomethoxyimino-2-(4-aminopyrimidin-2-yl)acetamido]-3-(1-pyridiniomethyl)-3-cephem-4-carboxylate (syn isomer).
mp 170° to 175° C. (dec.).
IR (Nujol): 3320, 3180, 1770, 1660, 1630, 1610, 1580, 1535 cm$^{-1}$.

(12) 7-[2-Ethoxyimino-2-(4-aminopyrimidin-2-yl)acetamido]-3-(3-formamido-1-pyridiniomethyl)-3-cephem-4-carboxylate (syn isomer).
mp 155° to 160° C. (dec.).
IR (Nujol): 3300, 3200, 1770, 1700–1520, 1500 cm$^{-1}$.

(13) 7-[2-Ethoxyimino-2-(4-aminopyrimidin-2-yl)acetamido]-3-(3-amino-1-pyridiniomethyl)-3-cephem-4-carboxylate (syn isomer).
mp 140° to 145° C. (dec.).
IR (Nujol): 3300, 3200, 1770, 1700–1600, 1580, 1540, 1510 cm$^{-1}$.

(14) 7-[2-Propargyloxyimino-2-(4-formamidopyrimidin-2-yl)acetamido]-3-(3-formamido-1-pyridiniomethyl)-3-cephem-4-carboxylate (syn isomer).
mp 144° to 151° C. (dec.).
IR (Nujol): 3250, 1770, 1690, 1610, 1570 cm$^{-1}$.

(15) 7-[2-Propargyloxyimino-2-(4-aminopyrimidin-2-yl)acetamido]-3-(3-amino-1-pyridiniomethyl)-3-cephem-4-carboxylate (syn isomer).
mp 140° to 155° C. (dec.).
IR (Nujol): 3350, 3200, 1770, 1630, 1585, 1510 cm$^{-1}$.

EXAMPLE 10

A mixture of 7-[2-methylthiomethoxyimino-2-(4-formamidopyrimidin-2-yl)acetamido]-3-(1-pyridiniomethyl)-3-cephem-4-carboxylate (syn isomer) (1.9 g) and concentrated hydrochloric acid (0.7 ml) in methanol (19 ml) was stirred for 1.5 hours at room temperature. The mixture was adjusted to pH 4 with aqueous sodium bicarbonate and evaporated under reduced pressure. The residue was dissolved in water (200 ml) and subjected to column chromatography on a non ionic adsorption resin "HP-20" (300 ml). After the column was washed with water, the elution was carried out with 25% aqueous methanol. The eluate was evaporated to remove methanol under reduced pressure and lyophilized to give 7-[2-methylthiomethoxyimino-2-(4-aminopyrimidin-2-yl)acetamido]-3-(1-pyridiniomethyl)-3-cephem-4-carboxylate (syn isomer) (1.13 g).
mp 170° to 175° C. (dec.).
IR (Nujol): 3320, 3180, 1770, 1660, 1630, 1610, 1580, 1535 cm$^{-1}$.
NMR (D$_2$O,δ): 2.20 (3H, s), 3.27 and 3.63 (2H, ABq, J=18 Hz), 5.28 (1H, d, J=5 Hz), 5.37 (2H, s), 5.37 and 5.60 (2H, ABq, J=14 Hz), 5.92 (1H, d, J=5 Hz), 6.60 (1H, d, J=6 Hz), 7.90–8.27 (3H, m), 8.40–8.77 (1H, m), 8.87–9.10 (2H, m).

EXAMPLE 11

The following compounds were obtained according to a similar manner to that of Example 10.

(1) 7-[2-Ethoxyimino-2-(4-aminopyrimidin-2-yl)acetamido]-3-(1-pyridiniomethyl)-3-cephem-4-carboxylate (syn isomer).
mp 155° to 160° C. (dec.).
IR (Nujol): 3320, 3190, 1770, 1660, 1610, 1580, 1540 cm$^{-1}$.

(2) 7-[2-Carboxymethoxyimino-2-(4-aminopyrimidin-2-yl)acetamido]-3-(1-pyridiniomethyl)-3-cephem-4-carboxylate (syn isomer).
mp 105° to 110° C. (dec.).
IR (Nujol): 3350, 3200, 1770, 1680–1570, 1200 cm$^{-1}$.

(3) 7-[2-Propargyloxyimino-2-(4-aminopyrimidin-2-yl)acetamido]-3-(3-amino-1-pyridiniomethyl)-3-cephem-4-carboxylate (syn isomer).
mp 140° to 155° C. (dec.).
IR (Nujol): 3350, 3200, 1770, 1630, 1585, 1510 cm$^{-1}$.

(4) 7-[2-Ethoxyimino-2-(4-aminopyrimidin-2-yl)acetamido]-3-(3-amino-1-pyridiniomethyl)-3-cephem-4-carboxylate (syn isomer).
mp 140° to 145° C. (dec.).
IR (Nujol): 3300, 3200, 1770, 1700–1600, 1580, 1540, 1510 cm$^{-1}$.

(5) 7-[2-Carboxymethoxyimino-2-(6-aminopyridin-2-yl)acetamido]-3-(1-pyridiniomethyl)-3-cephem-4-carboxylate (syn isomer).
mp 100° to 108° C. (dec.).
IR (Nujol): 3340, 3180, 1775, 1645, 1610 cm$^{-1}$.

EXAMPLE 12

7-[2-Propargyloxyimino-2-(4-aminopyrimidin-2-yl)acetamido]-3-(3-amino-1-pyridiniomethyl)-3-cephem-4-carboxylate (syn isomer) was obtained from 7-[2-propargyloxyimino-2-(4-formamidopyrimidin-2-yl)acetamido]-3-(3-formamido-1-pyridiniomethyl)-3-cephem-4-carboxylate (syn isomer) according to a similar manner to that of Example 10.

mp 140° to 155° C. (dec.).

IR (Nujol): 3350, 3200, 1770, 1630, 1585, 1510 cm⁻.

NMR (D₂O, δ): 2.99 (1H, t, J=2 Hz), 3.16 and 3.61 (2H, ABq, J=18 Hz), 4.90 (2H, d, J=2 Hz), 5.14 and 5.38 (2H, ABq, J=14 Hz), 5.26 (1H, d, J=5 Hz), 5.87 (1H, d, J=5 Hz), 6.55 (1H, d, J=6 Hz), 7.5–7.7 (2H, m), 7.9–8.2 (2H, m), 8.04 (1H, d, J=6 Hz).

EXAMPLE 13

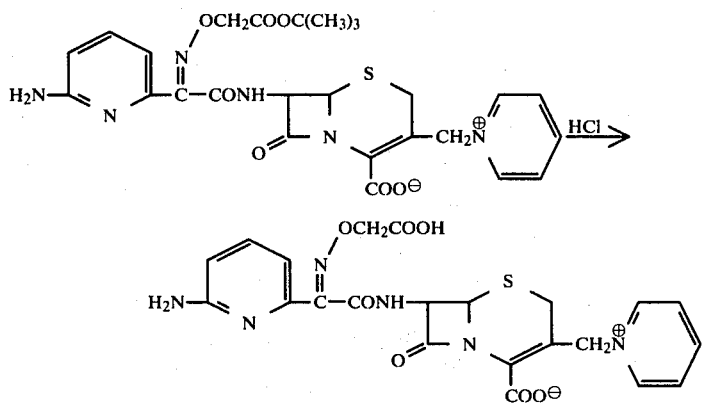

To a solution of 7-[2-tert-butoxycarbonylmethoxyimino-2-(6-aminopyridin-2-yl)acetamido]-3-(1-pyridiniomethyl)-3-cephem-4-carboxylate (syn isomer) (5.0 g) in formic acid (50 ml) was added conc. hydrochloric acid (2 ml), and the mixture was stirred at ambient temperature for an hour. After the solvent was removed by distillation under reduced pressure, the residue was dissolved in water (100 ml), followed by subjecting to column chromatography on a non-ionic adsorption resin, "Diaion HP-20" (200 ml). After the column was washed with water (600 ml), elution was carried out with 10% aqueous methanol. The eluates containing a desired compound were collected, evaporated to remove methanol under reduced pressure and then lyophilized to obtain 7-[2-carboxymethoxyimino-2-(6-aminopyridin-2-yl)acetamido]-3-(1-pyridiniomethyl)-3-cephem-4-carboxylate (syn isomer) (3.0 g), mp 100° to 108° C. (dec.).

IR (Nujol): 3340, 3180, 1775, 1645, 1610 cm⁻¹.

NMR (DMSO-d₆+D₂O, δ): 3.4 (2H, m), 4.65 (2H, s), 5.12 (1H, d, J=5 Hz), 5.4 (2H, m), 5.82 (1H, d, J=5 Hz), 6.57 (1H, d, J=8 Hz), 6.88 (1H, d, J=7 Hz), 7.48 (1H, dd, J=7 Hz, 8 Hz), 7.9–8.8 (3H, m), 9.28 (2H, m).

EXAMPLE 14

A mixture of 7-[2-t-butoxycarbonylmethoxyimino-2-(4-aminopyrimidin-2-yl)acetamido]-3-(1-pyridiniomethyl)-3-cephem-4-carboxylate (syn isomer) (1.31 g) and anisole (2.5 ml) in trifluoroacetic acid (7.5 ml) was stirred for 50 minutes under cooling in an ice-bath and for 70 minutes at room temperature. The mixture was poured into cold diisopropyl ether (60 ml) and the resulting precipitates were collected by filtration. The powder was dissolved in water (30 ml) and the mixture was adjusted to pH 4 to 5 with aqueous sodium bicarbonate and subjected to column chromatography on a non ionic adsorption resin "Diaion HP 20" (60 ml). After the column was washed with water, the elution was carried out with 30% aqueous methanol. The eluate was evaporated to remove methanol under reduced pressure and lyophilized to give 7-[2-carboxymethoxyimino-2-[4-aminopyrimidin-2-yl)acetamido]-3-(1-pyridiniomethyl)-3-cephem-4-carboxylate (syn isomer) (0.52 g).

mp 105° to 110° C.

IR (Nujol): 3350, 3200, 1770, 1680–1570, 1200 cm⁻¹.

NMR (DMSO-d₆+D₂O, δ): 3.00 and 3.50 (2H, ABq, J=18 Hz), 4.42 (2H, broad s), 5.00 (1H, d, J=5 Hz), 5.13 and 5.58 (2H, ABq, J=14 Hz), 5.70 (1H, d, J=5 Hz), 6.40 (1H, d, J=6 Hz), 7.8–8.2 (2H, m), 7.97 (1H, d, J=6 Hz), 8.4 (1H, m), 9.1 (2H, m).

EXAMPLE 15

A mixture of 7-[2-ethoxyimino-2-(4-aminopyrimidin-2-yl)acetamido]-3-(3-formamido-1-pyridiniomethyl)-3-cephem-4-carboxylate (syn isomer) (430 mg) and concentrated hydrochloric acid (0.16 ml) in methanol (4.3 ml) was stirred for 2 hours at room temperature. The mixture was adjusted to pH 4 with aqueous sodium bicarbonate and evaporated under reduced pressure. The residue was dissolved in water (50 ml) and subjected to column chromatography on a non ionic adsorption resin "HP-20" (70 ml). After the column was washed with water, the elution was carried out with 25% aqueous methanol. The eluate was evaporated to remove methanol under reduced pressure and lyophilized to give 7-[2-ethoxyimino-2-(4-aminopyrimidin-2-yl)acetamido]-3-(3-amino-1-pyridiniomethyl)-3-cephem-4-carboxylate (syn isomer) (0.22 g), mp 140° to 145° C. (dec.).

IR (Nujol): 3300, 3200, 1770, 1700–1600, 1580, 1540, 1510 cm⁻¹.

NMR (D₂O, δ): 1.33 (3H, t, J=7 Hz), 3.17 and 3.67 (2H, ABq, J=18 Hz), 4.42 (2H, q, J=7 Hz), 5.28 (1H, d, J=5 Hz), 5.0–5.73 (2H, m), 5.92 (1H, d, J=5 Hz), 6.63 (1H, d, J=6 Hz), 7.70 (2H, m), 8.12 (1H, d, J=6 Hz), 8.13 (2H, m).

EXAMPLE 16

The following compound was obtained according to a similar manner to that of Example 15. 7-[2-Propargyloxyimino-2-(4-aminopyrimidin-2-yl)acetamido]-3-

(3-amino-1-pyridiniomethyl)-3-cephem-4-carboxylate (syn isomer).

mp 140° to 155° C. (dec.).

IR (Nujol): 3350, 3200, 1770, 1630, 1585, 1510 cm$^{-1}$.

EXAMPLE 17

A mixture of 3-formamidopyridin (2.09 g), sodium iodide (15 g), sodium bicarbonate (0.72 g), phosphoric acid (0.504 g), water (2.5 ml) and acetonitrile (7.5 ml) was heated at 70° to 75° C. under stirring and 7-[2-propargyloxyimino-2-(4-formamidopyrimidin-2-yl)acetamido]cephalosporanic acid (syn isomer) (4.30 g) was added thereto. The mixture was stirred for 1.5 hours at the same temperature and diluted with water (80 ml). The aqueous solution was cooled, adjusted to pH 3.5 with 6 N hydrochloric acid and washed with ethyl acetate (150 ml), a mixed solution (150 ml) of chloroform and ethanol (2:1) and then chloroform (100 ml) successively. The aqueous solution was evaporated to remove organic solvent and subjected to column chromatography on a non ionic adsorption resin "Diaion HP 20" (110 ml). After the column was washed with water, the elution was carried out with 8% aqueous isopropanol. The eluate was evaporated to remove isopropanol under reduced pressure and lyophilized to give 7-[2-propargyloxyimino-2-(4-formamidopyrimidin-2-yl)acetamido]-3-(3-formamido-1-pyridiniomethyl)-3-cephem-4-carboxylate (syn isomer) (2.37 g).

mp 144° to 151° C. (dec.).

IR (Nujol): 3250, 1770, 1690, 1610, 1570 cm$^{-1}$.

NMR (D$_2$O, δ): 3.07 (1H, t, J=2 Hz), 3.25 and 3.77 (2H, ABq, J=18 Hz), 4.95 (2H, d, J=2 Hz), 5.33 (1H, d, J=5 Hz), 5.35 and 5.70 (2H, ABq, J=14 Hz), 5.95 (1H, d, J=5 Hz), 7.0–7.7 (1H, m), 7.9–8.3 (1H, m), 8.47 (1H, s), 8.63 (1H, d, J=6 Hz), 8.3–8.9 (2H, m), 9.0–9.3 (1H, m), 9.5 (1H, m).

EXAMPLE 18

A mixture of 7-[2-ethoxyimino-2-(4-aminopyrimidin-2-yl)acetamido]cephalosporanic acid (syn isomer) (1.02 g), sodium iodide (3.9 g), 3-formamidopyridine (493 mg), phosphoric acid (130 mg), sodium bicarbonate (185 mg), water (0.64 ml) and acetonitrile (1.9 ml) was stirred for 2 hours at 70° to 76° C. The reaction mixture was cooled, diluted with a mixture of water and ethyl acetate and adjusted to pH 3 with 6 N hydrochloric acid. The aqueous layer was separated out, washed with ethyl acetate, evaporated to remove ethyl acetate under reduced pressure and subjected to column chromatography on a non ionic adsorption resin "Diaion HP 20" (30 ml). After the column was washed with water, the elution was carried out with 20% aqueous methanol. The eluates containing an object compound were collected, evaporated to remove methanol under reduced pressure and lyophilized to give 7-[2-ethoxyimino-2-(4-aminopyrimidin-2-yl)acetamido]-3-(3-formamido-1-pyridiniomethyl)-3-cephem-4-carboxylate (syn isomer) (0.48 g), mp 155° to 160° C. (dec.).

IR (Nujol): 3300, 3200, 1770, 1700–1520, 1500 cm$^{-1}$.

NMR (D$_2$O+CD$_3$OD, δ): 1.33 (3H, t, J=7 Hz), 3.17 and 3.73 (2H, ABq, J=18 Hz), 4.40 (2H, q, J=7 Hz), 5.28 (1H, d, J=5 Hz), 5.28 and 5.72 (2H, ABq, J=14 Hz), 5.93 (1H, d, J=5 Hz), 6.62 (1H, d, J=6 Hz), 7.9–8.4 (1H, m), 8.13 (1H, d, J=6 Hz), 8.47 (1H, s), 8.43–8.93 (2H, m), 9.53 (1H, broad s).

EXAMPLE 19

The following compounds were obtained according to similar manners to those of Examples 17 and 18.

(1) 7-[2-Cyclopentyloxyimino-2-(4-aminopyrimidin-2-yl)acetamido]-3-(1-pyridiniomethyl)-3-cephem-4-carboxylate (syn isomer).

mp 165° to 180° C. (dec.).

IR (Nujol): 3300, 3200, 1770, 1670, 1620, 1580, 1340, 990, 770, 680 cm$^{-1}$.

(2) 7-[2-(2-Cyclopenten-1-yloxyimino)-2-(4-aminopyrimidin-2-yl)acetamido]-3-(1-pyridiniomethyl)-3-cephem-4-carboxylate (syn isomer), mp 160° to 175° C. (dec.).

IR (Nujol): 3300, 3200, 1770, 1660, 1620, 1580, 1540, 1360, 1150, 1100, 980, 770, 680 cm$^{-1}$.

(3) 7-[2-Cyclopentyloxyimino-2-(6-aminopyridin-2-yl)acetamido]-3-(1-pyridiniomethyl)-3-cephem-4-carboxylate (syn isomer).

mp 137° to 145° C. (dec.).

IR (Nujol): 3330, 3180, 1775, 1660, 1610 cm$^{-1}$.

(4) 7-[2-(2-Cyclopenten-1-yloxyimino)-2-(6-aminopyridin-2-yl)acetamido]-3-(1-pyridiniomethyl)-3-cephem-4-carboxylate (syn isomer).

mp 139° to 145° C. (dec.).

IR (Nujol): 3330, 3180, 1770, 1660, 1610 cm$^{-1}$.

(5) 7-[2-tert-Butoxycarbonylmethoxyimino-2-(6-aminopyridin-2-yl)acetamido]-3-(1-pyridiniomethyl)-3-cephem-4-carboxylate (syn isomer).

mp 94° to 104° C. (dec.).

IR (Nujol): 3340, 1770, 1670, 1610 cm$^{-1}$.

(6) 7-[2-Carboxymethoxyimino-2-(6-aminopyridin-2-yl)acetamido]-3-(1-pyridiniomethyl)-3-cephem-4-carboxylate (syn isomer).

mp 100° to 108° C. (dec.).

IR (Nujol): 3340, 3180, 1775, 1645, 1610 cm$^{-1}$.

(7) 7-[2-Ethoxyimino-2-(4-aminopyrimidin-2-yl)acetamido]-3-(1-pyridiniomethyl)-3-cephem-4-carboxylate (syn isomer).

mp 155° to 160° C. (dec.).

IR (Nujol): 3320, 3190, 1770, 1660, 1610, 1580, 1540 cm$^{-1}$.

(8) 7-[2-Methylthiomethoxyimino-2-(4-formamidopyrimidin-2-yl)acetamido]-3-(1-pyridiniomethyl)-3-cephem-4-carboxylate (syn isomer).

mp 150° to 155° C. (dec.).

IR (Nujol): 3200, 1775, 1680, 1605, 1565, 1480 cm$^{-1}$.

(9) 7-[2-Propargyloxyimino-2-(4-aminopyrimidin-2-yl)acetamido]-3-(1-pyridiniomethyl)-3-cephem-4-carboxylate (syn isomer).

mp 158° to 162° C. (dec.).

IR (Nujol): 3400–3150, 1770, 1670–1580, 1000 cm$^{-1}$.

(10) 7-[2-t-Butoxycarbonylmethoxyimino-2-(4-aminopyrimidin-2-yl)acetamido]-3-(1-pyridiniomethyl)-3-cephem-4-carboxylate (syn isomer).

mp 155° to 160° C. (dec.).

IR (Nujol): 3350, 3200, 1775, 1630, 1590, 1245, 1155 cm$^{-1}$.

(11) 7-[2-Carboxymethoxyimino-2-(4-aminopyrimidin-2-yl)acetamido]-3-(1-pyridiniomethyl)-3-cephem-4-carboxylate (syn isomer).

mp 105° to 110° C. (dec.).

IR (Nujol): 3350, 3200, 1770, 1680–1570, 1200 cm$^{-1}$.

(12) 7-[(2-Methylthiomethoxyimino-2-(4-aminopyrimidin-2-yl)acetamido]-3-(1-pyridiniomethyl)-3-cephem-4-carboxylate (syn isomer).
mp 170° to 175° C. (dec.).
IR (Nujol): 3320, 3180, 1770, 1660, 1630, 1610, 1580, 1535 cm$^{-1}$.

(13) 7-[2-Ethoxyimino-2-(4-aminopyrimidin-2-yl)-acetamido]-3-(3-amino-1-pyridiniomethyl)-3-cephem-4-carboxylate (syn isomer).
mp 140° to 145° C. (dec.).
IR (Nujol): 3300, 3200, 1770, 1700–1600, 1580, 1540, 1510 cm$^{-1}$.

(14) 7-[2-Propargyloxyimino-2-(4-aminopyrimidin-2-yl)acetamido]-3-(3-amino-1-pyridiniomethyl)-3-cephem-4-carboxylate (syn isomer).
mp 140° to 155° C. (dec.).
IR (Nujol): 3350, 3200, 1770, 1630, 1585, 1510 cm$^{-1}$.

What we claim is:
1. A compound of the formula:

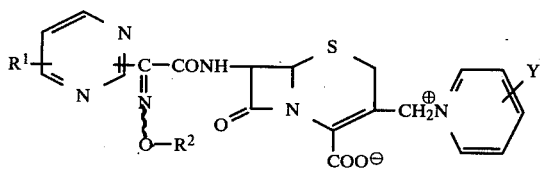

in which
R$^1$ is amino or a protected amino group,
R$^2$ is cyclo(lower)alkyl, cyclo(lower)alkenyl, lower alkyl, lower alkynyl, carboxy(lower)alkyl, protected carboxy(lower)alkyl or lower alkylthio(lower)alkyl, and
Y is hydrogen, amino or a protected amino group, and pharmaceutically acceptable salts thereof.

2. A compound of the formula:

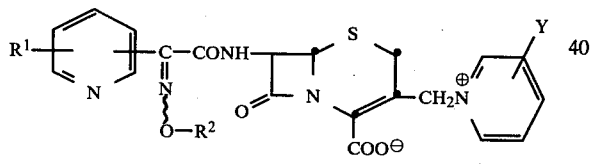

in which
R$^1$ is amino or a protected amino group,
R$^2$ is cyclo(lower)alkyl, cyclo(lower)alkenyl, lower alkyl, lower alkynyl, carboxy(lower)alkyl, protected carboxy(lower)alkyl or lower alkylthio(lower)alkyl, and
Y is hydrogen, amino or a protected amino group, and pharmaceutically acceptable salts thereof.

3. A compound of claim 2, wherein
R$^1$ is amino or lower alkanoylamino,
R$^2$ is cyclo(lower)alkyl, cyclo(lower)alkenyl, lower alkyl, lower alkynyl, carboxy(lower)alkyl, esterified carboxy(lower)alkyl or lower alkylthio(lower)alkyl, and Y is hydrogen, amino or lower alkanoylamino.

4. A pharmaceutical composition comprising, as an active ingredient, an effective amount of the compound of claim 2, in association with a non-toxic, pharmaceutically acceptable carrier or excipient.

5. A method for treating an infectious disease caused by pathogens, which comprises administering an effective amount of the compound of claim 2 to infected human beings and animals.

6. A compound of claim 1, wherein
R$^1$ is amino or lower alkanoylamino,
R$^2$ is cyclo(lower)alkyl, cyclo(lower)alkenyl, lower alkyl, lower alkynyl, carboxy(lower)alkyl, esterified carboxy(lower)alkyl or lower alkylthio(lower)alkyl, and Y is hydrogen, amino or lower alkanoylamino.

7. A compound of claim 6, wherein
R$^1$ is amino or formamido,
R$^2$ is cyclopentyl, 2-cyclopenten-1-yl, ethyl, propargyl, t-butoxycarbonylmethyl, methylthiomethyl or carboxymethyl, and
Y is hydrogen, amino or formamido.

8. A compound of claim 7, which is selected from the group consisting of:
7-[2-cyclopentyloxyimino-2-(4-aminopyrimidin-2-yl)acetamido]-3-(1-pyridiniomethyl)-3-cephem-4-carboxylate (syn isomer),
7-[2-(2-cyclopenten-1-yloxyimino)-2-(4-aminopyrimidin-2-yl)acetamido]-3-(1-pyridiniomethyl)-3-cephem-4-carboxylate (syn isomer),
7-[2-ethoxyimino-2-(4-aminopyrimidin-2-yl)acetamido]-3-(1-pyridiniomethyl)-3-cephem-4-carboxylate (syn isomer),
7-[2-propargyloxyimino-2-(4-aminopyrimidin-2-yl)acetamido]-3-(1-pyridiniomethyl)-3-cephem-4-carboxylate (syn isomer),
7-[2-carboxymethoxyimino-2-(4-aminopyrimidin-2-yl)acetamido]-3-(1-pyridiniomethyl)-3-cephem-4-carboxylate (syn isomer),
7-[2-methylthiomethoxyimino-2-(4-aminopyrimidin-2-yl)acetamido]-3-(1-pyridiniomethyl)-3-cephem-4-carboxylate (syn isomer),
7-[2-propargyloxyimino-2-(4-aminopyrimidin-2-yl)acetamido]-3-(3-amino-1-pyridiniomethyl)-3-cephem-4-carboxylate (syn isomer) and
7-[2-ethoxyimino-2-(4-aminopyrimidin-2-yl)acetamido]-3-(3-amino-1-pyridiniomethyl)-3-cephem-4-carboxylate (syn isomer).

9. A compound of claim 3, wherein
R$^1$ is amino or lower alkanoylamino,
R$^2$ is cyclo(lower)alkyl, cyclo(lower)alkenyl, carboxy(lower)alkyl or lower alkoxycarbonyl(lower)alkyl, and
Y is hydrogen.

10. A compound of claim 9, wherein
R$^1$ is amino or formamido, and
R$^2$ is cyclopentyl, 2-cyclopenten-1-yl, carboxymethyl or t-butoxycarbonylmethyl.

11. A compound of claim 10, which is selected from the group consisting of:
7-[2-cyclopentyloxyimino-2-(6-aminopyridin-2-yl)acetamido]-3-(1-pyridiniomethyl)-3-cephem-4-carboxylate (syn isomer),
7-[2-(2-cyclopenten-1-yloxyimino)-2-(6-aminopyridin-2-yl)acetamido]-3-(1-pyridiniomethyl)-3-cephem-4-carboxylate (syn isomer),
7-[2-t-butoxycarbonylmethoxyimino-2-(6-aminopyridin-2-yl)acetamido]-3-(1-pyridiniomethyl)-3-cephem-4-carboxylate (syn isomer) and
7-[2-carboxymethoxyimino-2-(6-aminopyridin-2-yl)acetamido]-3-(1-pyridiniomethyl)-3-cephem-4-carboxylate (syn isomer).

12. A pharmaceutical composition comprising, as an active ingredient, an effective amount of the compound of claim 1, in association with a non-toxic, pharmaceutically acceptable carrier or excipient.

13. A method for treating an infectious disease caused by pathogens, which comprises administering an effective amount of the compound of claim 1 to infected human beings and animals.

* * * * *